US012678619B2

(12) United States Patent
Zimmerling

(10) Patent No.: US 12,678,619 B2
(45) Date of Patent: Jul. 14, 2026

(54) HOLDING MAGNETS AND MAGNET SYSTEM FOR IMPLANTABLE SYSTEMS OPTIMIZED FOR MRI

(71) Applicant: MED-EL Elektromedizinische Geraete GmbH, Innsbruck (AT)

(72) Inventor: Martin Zimmerling, Patsch (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 187 days.

(21) Appl. No.: 18/795,177

(22) Filed: Aug. 5, 2024

(65) Prior Publication Data

US 2025/0050099 A1 Feb. 13, 2025

Related U.S. Application Data

(63) Continuation of application No. 17/462,903, filed on Aug. 31, 2021, now Pat. No. 12,053,629.

(Continued)

(51) Int. Cl.
| | |
|---|---|
| *A61N 1/36* | (2006.01) |
| *A61N 1/08* | (2006.01) |
| *A61N 1/372* | (2006.01) |

(52) U.S. Cl.
CPC ......... *A61N 1/086* (2017.08); *A61N 1/36038* (2017.08); *A61N 1/37223* (2013.01)

(58) Field of Classification Search
CPC .. A61N 1/375; A61N 1/3758; A61N 1/37223; A61N 1/37229; A61N 1/36038; A61N 1/36036; A61N 1/36039
See application file for complete search history.

(56) References Cited

U.S. PATENT DOCUMENTS

| | | | |
|---|---|---|---|
| 6,348,070 | B1 | 2/2002 | Teissl et al. |
| 7,566,296 | B2 | 7/2009 | Zimmerling et al. |

(Continued)

FOREIGN PATENT DOCUMENTS

| | | |
|---|---|---|
| AT | E467405 | 5/2010 |
| AT | E543346 | 2/2012 |

(Continued)

OTHER PUBLICATIONS

Notice of Acceptance in Australian Application No. 2021225130 dated Jan. 3, 2024, 4 pages.

(Continued)

*Primary Examiner* — George R Evanisko
(74) *Attorney, Agent, or Firm* — Barclay Damon LLP

(57) ABSTRACT

An implant device is disclosed that includes signal processing circuitry configured to receive an implant communications signal transmitted from an external transmitting coil, a magnet case configured to be rotatable about a case rotation axis, and an implant magnet arrangement within the magnet case configured to cooperate with an external holding magnet in an external device to magnetically hold the external device against overlying skin. The implant magnet arrangement includes a plurality of cylindrical magnets, each with a center cylinder axis perpendicular to the case rotation axis, and each configured to be rotatable about a center cylinder axis. The north and south magnetic poles are arranged with respect to each other so as not to lie on a common diameter through the center cylinder axis such that the north and south magnetic directions form a magnetic angle less than 180 degrees with a vertex at the center cylinder axis.

24 Claims, 15 Drawing Sheets

Related U.S. Application Data

(60) Provisional application No. 63/075,912, filed on Sep. 9, 2020.

(56) References Cited

U.S. PATENT DOCUMENTS

| | | | |
|---|---|---|---|
| 8,634,909 B2 | 1/2014 | Zimmerling et al. | |
| 8,733,494 B1 | 5/2014 | Leigh et al. | |
| 9,872,993 B2 | 1/2018 | Zimmerling | |
| 10,532,209 B2 | 1/2020 | Lee et al. | |
| 10,744,333 B2 | 8/2020 | Hillbratt et al. | |
| 10,806,936 B2 | 10/2020 | Crawford et al. | |
| 11,071,869 B2 | 7/2021 | Leigh et al. | |
| 11,090,498 B2 | 8/2021 | Gibson et al. | |
| 11,097,095 B2 | 8/2021 | Smith et al. | |
| 11,364,384 B2 | 6/2022 | Smith et al. | |
| 11,476,025 B2 | 10/2022 | Lee et al. | |
| 11,883,662 B2 | 1/2024 | Andersson et al. | |
| 2011/0022120 A1 | 1/2011 | Ball et al. | |
| 2018/0133486 A1 | 5/2018 | Smith et al. | |
| 2018/0146308 A1 | 5/2018 | Leigh et al. | |
| 2018/0279061 A1 | 9/2018 | Walraevens et al. | |
| 2019/0076649 A1 | 3/2019 | Lee et al. | |
| 2021/0156934 A1 | 5/2021 | Smith et al. | |
| 2021/0234265 A1 | 7/2021 | Smith et al. | |
| 2022/0032048 A1 | 2/2022 | Von Huben | |
| 2022/0273948 A1 | 9/2022 | Calixto et al. | |
| 2022/0331598 A1* | 10/2022 | Isaacson | A61N 1/36038 |
| 2023/0115968 A1 | 4/2023 | Lee et al. | |

FOREIGN PATENT DOCUMENTS

| | | |
|---|---|---|
| AU | 2014200384 | 2/2014 |
| CA | 2478324 | 10/2003 |
| CN | 113244531 | 8/2021 |
| CN | 217187481 | 8/2022 |
| CN | 116469638 | 7/2023 |
| CN | 116474260 | 7/2023 |
| EP | 0984664 | 3/2000 |
| EP | 2853287 | 4/2015 |
| EP | 2925018 | 9/2015 |
| EP | 2560730 | 11/2016 |
| KR | 20200078292 | 7/2020 |
| RU | 193952 | 11/2019 |
| RU | 196686 | 3/2020 |
| RU | 198574 | 7/2020 |
| RU | 2729443 | 8/2020 |
| WO | 2001039830 | 6/2001 |
| WO | 2003092326 | 11/2003 |
| WO | 2004114723 | 12/2004 |
| WO | 2007095196 | 8/2007 |
| WO | 2008014245 | 1/2008 |
| WO | 2008109800 | 9/2008 |
| WO | 2009149069 | 12/2009 |
| WO | 2010068730 | 6/2010 |
| WO | 2010133702 | 11/2010 |
| WO | 2011011409 | 1/2011 |
| WO | 2011022356 | 2/2011 |
| WO | 2011068822 | 6/2011 |
| WO | 2011109486 | 9/2011 |
| WO | 2011113468 | 9/2011 |
| WO | 2012116130 | 8/2012 |
| WO | 2013043176 | 3/2013 |
| WO | 2013054312 | 4/2013 |
| WO | 2013096559 | 6/2013 |
| WO | 2014008169 | 1/2014 |
| WO | 2014011441 | 1/2014 |
| WO | 2014179274 | 11/2014 |
| WO | 2016190886 | 12/2016 |
| WO | 2016199096 | 12/2016 |
| WO | 2017007780 | 1/2017 |
| WO | 2017027045 | 2/2017 |
| WO | 2017027046 | 2/2017 |
| WO | 2017034530 | 3/2017 |
| WO | 2017044523 | 3/2017 |
| WO | 2017105510 | 6/2017 |
| WO | 2017105604 | 6/2017 |
| WO | 2017172566 | 10/2017 |
| WO | 2018193400 | 10/2018 |
| WO | 2018200347 | 11/2018 |
| WO | 2019027745 | 2/2019 |
| WO | 2020092185 | 5/2020 |
| WO | 2020174330 | 9/2020 |
| WO | 2020212849 | 10/2020 |
| WO | 2021255538 | 12/2021 |
| WO | 2022038534 | 2/2022 |
| WO | 2023012599 | 2/2023 |
| WO | 2023021357 | 2/2023 |
| WO | 2023063934 | 4/2023 |
| WO | 2023113790 | 6/2023 |
| WO | 2023119156 | 6/2023 |

OTHER PUBLICATIONS

Extended European Search Report in Application No. 21194598.5 dated Jan. 28, 2022, 4 pages.

Search Report in EP Application No. 202192120 dated Feb. 18, 2022, 1 page.

* cited by examiner

HOLDING MAGNETS AND MAGNET SYSTEM FOR IMPLANTABLE SYSTEMS OPTIMIZED FOR MRI

CROSS-REFERENCE TO RELATED APPLICATIONS

This application is a continuation of U.S. patent application Ser. No. 17/462,903 filed on Aug. 31, 2021, which claims priority from U.S. Provisional Patent Application 63/075,912 filed on Sep. 9, 2020, the disclosures of which are incorporated herein by reference in their entirety.

FIELD OF THE INVENTION

The present invention relates to at least partially implantable devices such as partly implantable hearing devices, for example cochlear implants, and specifically, to implantable magnets for interaction with external magnets in such devices.

BACKGROUND ART

Some hearing implants such as Middle Ear Implants (MEI's) and Cochlear Implants (CI's) employ cooperating attachment magnets located in the implant and the external part to magnetically hold the external part in place over the implant. For example, as shown in FIG. 1, a typical cochlear implant system may include an external transmitter device 101 containing transmitting coil 102 and an external attachment magnet 103. The external attachment magnet 103 has a conventional cylindrical disc-shape and a north-south magnetic dipole having an axis that is perpendicular to the skin of the patient to produce external magnetic field lines 104 as shown. Implanted under the patient's skin is a corresponding receiver assembly 105 having similar receiving coil 106 and an implant magnet 107. The implant magnet 107 also has a cylindrical disc-shape and a north-south magnetic dipole having a magnetic axis that is perpendicular to the skin of the patient to produce internal magnetic field lines 108 as shown. The internal receiver device 105 is surgically implanted and fixed in place within the patient's body. The external transmitter device 101 is placed in proper position over the skin covering the internal receiver assembly 105 and held in place by interaction between the internal magnetic field lines 108 and the external magnetic field lines 104. Rf signals from the transmitter coil 102 couple data and/or power to the receiving coil 106 which is in communication with an implanted processor module (not shown).

One problem arises when the patient undergoes Magnetic Resonance Imaging (MRI) examination. Interactions occur between the implant magnet and the applied external magnetic field for the MRI. As shown in FIG. 2, the direction of the magnetization $\overline{m}$ of the implant magnet 202 is essentially perpendicular to the skin of the patient. In this example, the strong static magnetic field $\overline{B}$ from the MRI creates a torque $\overline{T}$ on the internal magnet 202, which may displace the internal magnet 202 or the whole implant device 201 out of proper position. Among other things, this may damage the adjacent tissue in the patient. In addition, the external magnetic field $\overline{B}$ from the MRI may reduce or remove the magnetization $\overline{m}$ of the implant magnet 202 so that it may no longer be strong enough to hold the external transmitter device in proper position. The implant magnet 202 also may cause imaging artifacts in the MRI image, there may be induced voltages in the receiving coil, and hearing artifacts due to the interaction of the external magnetic field $\overline{B}$ of the MRI with the implanted device. Torque and forces acting on the implant magnet and demagnetization of the implant magnet are especially an issue with MRI field strengths at 1.5 Tesla and higher.

Thus, for many existing implant systems with magnet arrangements, it is common to either not permit MRI, or limit use of MRI to lower field strengths. Other existing solutions include use of a surgically removable magnets, spherical implant magnets (e.g. U.S. Pat. No. 7,566,296, incorporated herein by reference in its entirety), and various ring magnet designs (e.g., U.S. Patent Publication 2011/0022120 incorporated herein by reference in its entirety).

U.S. Pat. No. 8,634,909 (incorporated herein by reference in its entirety) discloses an implant magnet having a magnetic dipole moment direction that is parallel to the end surfaces of a disc-shaped implant magnet—that is, perpendicular to the conventional magnetic dipole moment direction of a disc-shaped implant magnet. The magnet is then held in a magnet receptacle that allows the magnet to rotate about its center axis in response to an external magnetic field such as from an MRI to realign and minimize creating torque.

It also has been suggested to use a set of multiple cylindrical magnets which have a magnetization direction perpendicular to the rotation axis of the cylinder and rotatable about the rotation axis embedded into a magnet frame and case which can rotate around the central axis of the case (see e.g., WO2017/105510, which is incorporated herein by reference in its entirety). In that approach two or more diametrically-magnetized cylindrical magnets align in a configuration where one north pole is oriented next to an adjacent south pole and vice versa when no external magnetic field is present. In this configuration, the cylindrical magnets together behave like a single disc-shaped magnet as disclosed in the '909 patent with magnetization direction parallel to the skin surface—unless a very strong external magnetic field is applied —, but due to a relatively poor filling factor have only a small combined magnet volume, thus requiring an extra-large or extra-strong external magnet.

SUMMARY OF THE EMBODIMENTS

In accordance with one embodiment of the invention, an implantable hearing implant includes an implant device containing signal processing circuitry configured to receive an implant communications signal transmitted from an external transmitting coil through overlying skin of a patient. The implant device includes an outermost surface adapted to lie between the overlying skin and underlying skull bone of the patient. The implantable hearing implant further includes a magnet case within the implant device. The magnet case is configured to be rotatable about a case rotation axis which is at least approximately perpendicular to the outermost surface of the implant device. The implantable hearing implant further includes an implant magnet arrangement within the magnet case configured to cooperate with an external holding magnet in an external device to be located over the overlying skin to magnetically hold the external device against the overlying skin. The implant magnet arrangement includes one or more cylindrical magnets, each cylindrical magnet having a center cylinder axis perpendicular to the case rotation axis, configured to be rotatable about the center cylinder axis, and having an outer cylindrical surface with a north magnetic pole and a south magnetic pole. A north magnetic direction is defined by a radial vector extending from the center cylinder axis to the north magnetic pole and a south magnetic direction is defined by a radial vector extending from the south magnetic pole to the center cylinder axis. The north magnetic pole and the south magnetic pole are arranged with respect to each other so as not to lie on a common diameter through the center cylinder axis such that the north magnetic direction and the south magnetic direction form a magnetic angle less than 180 degrees with a vertex at the center cylinder axis.

In some embodiments, the implant magnet arrangement may include a plurality of cylindrical magnets configured to magnetically align with respect to each other to create a common line of magnetic flux through the plurality of cylindrical magnets, the magnet case, and the overlying skin to cooperate with the external holding magnet. The implantable hearing implant further includes one or more diametrically magnetized supplemental cylindrical magnets between the plurality of cylindrical magnets configured to couple the common line of magnetic flux between the plurality of cylindrical magnets. The implantable hearing implant further includes soft magnetic material between the plurality of cylindrical magnets configured to couple the common line of magnetic flux between the plurality of cylindrical magnets. The implant magnet arrangement may be configured to respond to a strong external magnetic field by rotation of the magnet case about the case rotation axis and rotation of the cylindrical magnets about their respective center cylinder axes so as to minimize net torque imparted to the implant device. The magnetic angle may be between 90 degrees and 140 degrees. Each cylindrical magnet may be configured to be fully rotatable about the center cylinder axis through a complete rotation range of 360 degrees. Each cylindrical magnet may be configured to be limitedly rotatable about the center cylinder axis through a limited rotation range of less than 180 degrees. The limited rotation range may be 90 degrees.

In accordance with another embodiment of the invention, an implantable hearing implant includes an implant device containing signal processing circuitry configured to receive an implant communications signal transmitted (e.g. from an external transmitting coil) through overlying skin of a patient. The implant device includes an outermost surface implantable hearing implant includes adapted to lie between the overlying skin and underlying skull bone and at least approximately parallel to the skin of the patient. The implantable hearing implant further includes an implant magnet configured to cooperate with an external holding magnet in an external device to be located over the overlying skin to magnetically hold the external device against the overlying skin. The implant magnet has a north magnetic pole, a south magnetic pole, and as a whole has an overall magnetic dipole moment that is parallel to or at an angle of 30° or less with respect to the outermost surface. The implant magnet also has a north end portion including the north magnetic pole and a south end portion including the south magnetic pole, the north and south end portions each being formed from permanent magnetic material and each having an individual magnetic dipole moment that is inclined with respect to the overall magnetic dipole moment. The individual magnetic dipole moment in the north end portion is inclined with respect to the overall magnetic dipole moment so as to have a component pointing towards the outermost surface. The individual magnetic dipole moment in the south end portion is inclined with respect to the overall magnetic dipole moment such as to have a component pointing away from the outermost surface. The north and south end portions of the implant magnet may be fixedly attached directly with each other, or may each be fixedly attached to an intermediate portion of said implant magnet.

According to the second embodiment of the invention, the implant magnet "as a whole" has an "overall magnetic dipole moment" which is at least approximately parallel to the outermost surface, or in other words, approximately parallel to the skin in the implanted state. As the skilled person will appreciate, the magnetic dipole moment m of a magnetic body as a whole is a macroscopic quantity defining the "strength" of the magnetic dipole. When arranged in an external magnetic field having a flux density B, a torque $\tau$ is generated that corresponds to the vector product of the magnetic dipole moment m and the flux density B, i.e. $\tau = m \times B$. Accordingly, the overall magnetic dipole moment m of the implant magnet can be readily determined when placed in an external magnetic field: the implant magnet will orient itself to bring the dipole moment m in alignment with the flux density B of the external magnetic field, thereby revealing the direction of the magnetic dipole moment m, while its magnitude is defined by the size of the torque needed to rotate the implant magnet out of this alignment. The magnetic dipole moment of the implant magnet as a whole determines how the internal magnet reacts to the external magnetic field in an MRI device.

In some embodiments, the implant magnet has north and a south end portions including the north and south magnetic poles, respectively, each having an individual magnetic dipole moment that is inclined with respect to the overall magnetic dipole moment. In these north and south end portions, the respective magnetizations are hence not aligned with the overall magnetic dipole moment of the implant magnet as a whole. The magnetization of a material is designated as a vector field M that expresses the density of magnetic dipole moments in the magnetic material, i.e.

$$M = \frac{dm}{dV},$$

where dm is the elementary magnetic moment and dV is the corresponding volume element. In other words, the magnetic moment m associated with a magnet is the space integral of the magnetization M over the magnet's volume, i.e. $M = \iiint M \, dV$. As used herein, a "vector" is simply understood as a physical object that has a magnitude and a direction. No distinction between vectors and pseudovectors according to their transformation properties is made herein. Vectors are generally represented by symbols in bold font.

In some embodiments, the north and south end portions are each formed from permanent magnetic material. A "permanent magnetic material" as understood herein has a broad meaning, but is in any case distinguished from magnetic soft materials such as soft iron as it is used in the art for pole shoes or the like. In particular, the permanent magnetic material in the north and south end portions should have an intrinsic magnetic coercivity $H_{Ci}$ of more than 200 A/m, preferably of more than 500 A/m, more preferably more than 800 A/m and most preferably more than 1000 A/m. The individual magnetic dipole moment in the north end portion has a component pointing towards the outermost surface, and the individual magnetic dipole moment in the south end portion has a component pointing away from the outermost surface. The inventor has found that this way, the magnetic attraction or holding force applied to an external magnet of an external device can be significantly increased as compared to a prior art implant magnet of same size and material which is homogeneously magnetized in a direction parallel to the skin throughout its volume, while still allowing for an overall magnetic moment that is parallel to the skin.

In some embodiments, the implant magnet may be rotatable around a rotation axis that is perpendicular to the outermost surface, or may deviate from perpendicular by less than 30°, wherein in each available rotational position of the implant magnet upon rotation around the rotation axis, the overall magnetic dipole moment is parallel to or at an angle of 30° or less with respect to the outermost surface. The implant magnet may have a shape that is rotationally symmetric around the rotation axis. The implant magnet may have an outer end surface facing the outermost surface of the implant device and an inner end surface facing away from the outermost surface, wherein one or both of the inner and outer end surfaces are perpendicular to the rotation axis. For example, the implant magnet may have a disc shape. The implant magnet may have a planar outer end surface, to optimally make use of the limited space in the implant device. An angle of inclination between each individual magnetic dipole moment in the north and south end portions with respect to the overall magnetic dipole moment may be ≤50°. This will allow for safely avoiding a situation in which the implant magnet could be inadvertently weakened or de-magnetized in a strong external MRI field in case the patient does not hold his or her head straight during the MRI procedure, but for example tilted to one side by e.g. up to 30°. The implant magnet may have an average diameter dI in a direction parallel to the overall magnetic dipole moment and an average thickness hI in a direction perpendicular to the outermost surface, wherein in one or both of the north and south end portions, the individual magnetic dipole moment is inclined with respect to the overall magnetic dipole moment by an angle α, wherein $$\arctan(hI/(dI/2)) - 15° \le \alpha \le \arctan(hI/(dI/2)) + 7°, \text{ or}$$
$$\arctan(hI/(dI/2)) - 10° \le \alpha \le \arctan(hI/(dI/2)) + 5°.$$

Herein, the angle α is measured in a plane that is perpendicular to the outermost surface. This angular range has been found to allow for a particularly good increase in the attachment force. For larger angles α, the distance between the north and south poles would decrease, which in turn would lead to an excessive decrease in holding force with distance from the implant magnet.

In some embodiments, the north and south end portions may be directly adjacent with each other, and each form one of two halves of the implant magnet. This embodiment leads to very good holding forces, and at the same time allows for comparatively easy manufacture. Alternatively, the north and south end portions of the implant magnet are separated from each other by an intermediate portion having an individual magnetic dipole moment that is parallel to the overall magnetic dipole moment, or deviates from parallel by less than 10°, preferably less than 5°. This embodiment allows for comparatively large inclinations of the magnetization in the north and south end portions while at the same time avoiding magnetic short-circuits at the outer surface, thereby leading to very good holding forces.

In some embodiments, one or both of the north and south end portions of the implant magnet may have an outer section closer to the outermost surface and an inner section further away from the outermost surface, wherein an angle of inclination of the individual magnetic dipole moment with respect to the overall magnetic dipole moment in the outer section is less than in the inner section. This embodiment allows for an improved magnetic flux within the implant magnet while avoiding the distance of the north and south poles to decrease.

In some embodiments, the implant magnet may have an outer end surface facing the outermost surface of the implant device and an inner end surface facing away from the outermost surface, wherein a middle plane is defined to be located at an equal distance from the outer and inner end surfaces, and wherein the implant magnet fulfils one or both of the following criteria (i) and (ii):

(i) at least 55%, preferably at least 65%, of the total magnetic flux of a magnetic field generated outside of the implant magnet when placed in isolation in air or a vacuum is located on a side of the middle plane at which the outermost surface is located in the assembled state, (ii) more than 50%, or preferably more than 55% of the mass of the implant magnet is located on a side of the middle plane at which the outermost surface is located, wherein the edges of the implant magnet at the inner end surface are chamfered. Criterion (i) defines the distribution of the magnetic flux generated by the implant magnet itself, i.e. when placed in isolation in air or vacuum. According to this criterion, the larger part of the magnetic flux is on one side of the middle plane, and this side is the side on which in the "assembled state", i.e. when the implant magnet is arranged in the implant device, the outermost surface of the implant device would be located. In other words, the implant magnet is devised so that by itself it already generates the bigger part of its flux in the region where it is needed for establishing an attractive holding force with an external device, i.e. more to the outside than to the inside of the body. The second criterion (ii) specifies that more than half of the mass of the implant magnet is located on the side of the middle plane at which the outermost surface located. This again helps with generating the magnetic flux closer to the outside region than the inside region with respect to the implant magnet. One way of reducing the mass of the implant magnet towards the inside of the middle plane is by providing for chamfered edges at the inner end surface of the implant magnet. This shape also allows for a more favorable magnetic flux.

In some embodiments, the north and south end portions of the external magnet are formed from anisotropic magnet elements each having a preferred magnetization direction, wherein the anisotropic magnet elements are joined with each other or with an intermediate portion arranged in between, wherein the preferred magnetization directions are arranged at an angle with respect to the overall dipole moment of the external magnet as a whole. The anisotropic magnet elements can e.g. be made by applying an external magnetic field while the magnet is formed, which may for example involve sintering. The anisotropic magnets have the advantage that they allow for higher magnetizations in their final state. The anisotropic magnets will not have their final magnetic strength after manufacture yet, but will only acquire it after a final magnetization using a strong magnetic pulse. While an isotropic magnet can be magnetized by a strong magnetic pulse in any direction, the anisotropic magnets can only be magnetized in their preferred magnetization directions established upon manufacture. This is actually an advantage in the manufacturing process of the magnet as a whole, because the magnet can be assembled from anisotropic magnet elements with the preferred magnetization directions in the north and south end portions inclined with respect to the overall magnetization direction, but before the anisotropic magnet elements are fully magnetized. This makes the handling of the anisotropic magnet elements prior to the assembly, as well as the joining of the magnet elements much easier. It is then possible to fully magnetize the anisotropic magnet elements in the joint state by applying an external magnetic pulse aligned with the direction of the eventual overall magnetic dipole moment. During this magnetization process, the magnetization directions of the anisotropic magnet elements as part of the entire implant magnet will be preserved, while their strength will be increased.

In some embodiments, the implant magnet may have on at least part of the inner end surface (913) a layer of magnetic soft material, such as for example soft iron, applied. This may help to shield a magnetic field generated by the implant magnet itself toward the inside of the body and thereby may reduce artefacts during MRI-scanning. The implant magnet may be a rare earth magnet, e.g., a rare earth magnet including neodymium, samarium, terbium, dysprosium and/or holmium.

In accordance with another embodiment of the invention, an implant system includes an implantable hearing device according to one of the preceding embodiments and an external device including signal processing circuitry configured to transmit an implant communications signal to the implantable hearing device. The external device includes an innermost surface adapted to lie adjacent to the overlying skin and an external magnet or magnet assembly in the external device to be located over the overlying skin and magnetically configured to cooperate with the implant magnet of the implantable hearing device so as to hold the external device against the overlying skin.

The external magnet may be similar to the implant magnet, but may also be of a different design. In particular, since the external device can be taken off prior to an MRI procedure, the external magnet does not have to be specifically designed to cope with strong external MRI magnetic fields. Accordingly, the external magnet may be an arrangement of two magnets having magnetic dipole moments arranged perpendicular to the innermost surface of the external device, and hence to the skin, with their north and south poles arranged adjacent to the south and north poles of the implant magnet, respectively.

In some embodiments, the external magnet or magnet arrangement may have a north magnetic pole, a south magnetic pole, and may further as a whole have an overall magnetic dipole moment that is parallel to or at an angle of 30° or less with respect to the innermost surface of the external device. The external magnet may be of a similar design as disclosed in one of the embodiments with respect to the internal magnet above. The external magnet may have a north end portion including the north magnetic pole and a south end portion including the south magnetic pole, the north and south end portions each being formed from permanent magnetic material and each having an individual magnetic dipole moment that is inclined with respect to the overall magnetic dipole moment of the external magnet. The individual magnetic dipole moment in the north end portion may have a component pointing towards the innermost surface of the external device, and the individual magnetic dipole moment in the south end portion may have a component pointing away from the innermost surface of the external device.

In some embodiments, the external magnet is rotatable around a rotation axis that is perpendicular to the innermost surface of the external device or deviates from perpendicular by less than 30°, wherein in each available rotational position of the external magnet upon rotation around the rotation axis, the overall magnetic dipole moment is parallel to or at an angle of 30° or less with respect to the innermost surface, wherein the external magnet has a shape that is rotationally symmetric around its rotation axis. The external magnet may have a planar inner end surface facing the innermost surface of the external device.

In some embodiments, the external magnet may have an average diameter $d_E$ in a direction parallel to the overall magnetic dipole moment and an average thickness $h_E$ in a direction perpendicular to the innermost surface of the external device, wherein in one or both of the north and south end portions, the individual magnetic dipole moment is inclined with respect to the overall magnetic dipole moment by an angle $\alpha$, wherein $$\arctan\left(h_E/\left(d_E/2\right)\right) - 15° \le \alpha \le \arctan\left(h_E/\left(d_E/2\right)\right) + 7°, \text{ preferably}$$
$$\arctan\left(h_E/\left(d_I/2\right)\right) - 10° \le \alpha \le \arctan\left(h_E/\left(d_E/2\right)\right) + 5°.$$

The advantages of these angular ranges are similar to those explained above with reference to the implant magnet. Similar to the case of the implant magnet, the angle $\alpha$ is measured in a plane that is perpendicular to the innermost surface of the external device, or in other words, in a plane that is at least approximately perpendicular to the skin.

In some embodiments, the north and south end portions of the external magnet are directly adjacent with each other, and in particular each form one of two halves of the external magnet. Alternatively, the north and south end portions of the external magnet are separated from each other by an intermediate portion having an individual magnetic dipole moment that is parallel to the overall magnetic dipole moment of the external magnet or deviates from parallel by less than 10°, preferably less than 5°.

In some embodiments, one or both of the north and south end portions of the implant magnet may have an inner section closer to the innermost surface of the external device and an outer section further away from the innermost surface of the external device, wherein an angle of inclination of the individual magnetic dipole moment with respect to the overall magnetic dipole moment in the inner section is less than in the outer section. The external magnet may have an inner end surface facing the innermost surface of the external device and an outer end surface facing away from the innermost surface of the external device. A middle plane is defined to be located at equal distance from the outer and inner end surfaces of the external device. The external magnet may fulfil one or both of the following criteria (i) and (ii):

(i) at least 55%, preferably at least 65% of the total magnetic flux of a magnetic field generated outside of the external magnet when placed in isolation in air or a vacuum is located on a side of the middle plane at which the innermost surface of the external device is located in the assembled state, (ii) more than 50%, preferably more than 55% of the mass of the external magnet is located on a side of the middle plane at which the innermost surface is located, wherein in particular, the edges of the external magnet at the inner end surface are chamfered.

In some embodiments, the north and south end portions of the external magnet are formed from anisotropic magnet elements each having a preferred magnetization direction, wherein the anisotropic magnet elements are joined with each other or with an intermediate portion arranged in between, wherein the preferred magnetization directions are arranged at an angle with respect to the overall dipole moment of the external magnet as a whole. The external magnet may be a rare earth magnet, e.g., a rare earth magnet including neodymium, such as neodymium-ion-boron magnets, and/or including samarium, such as samarium-cobalt magnets, and/or including terbium, dysprosium, holmium or combinations thereof.

Embodiments of the present invention also include a hearing implant system containing a magnet arrangement according to any of the foregoing.

10

Figures 16, 17:
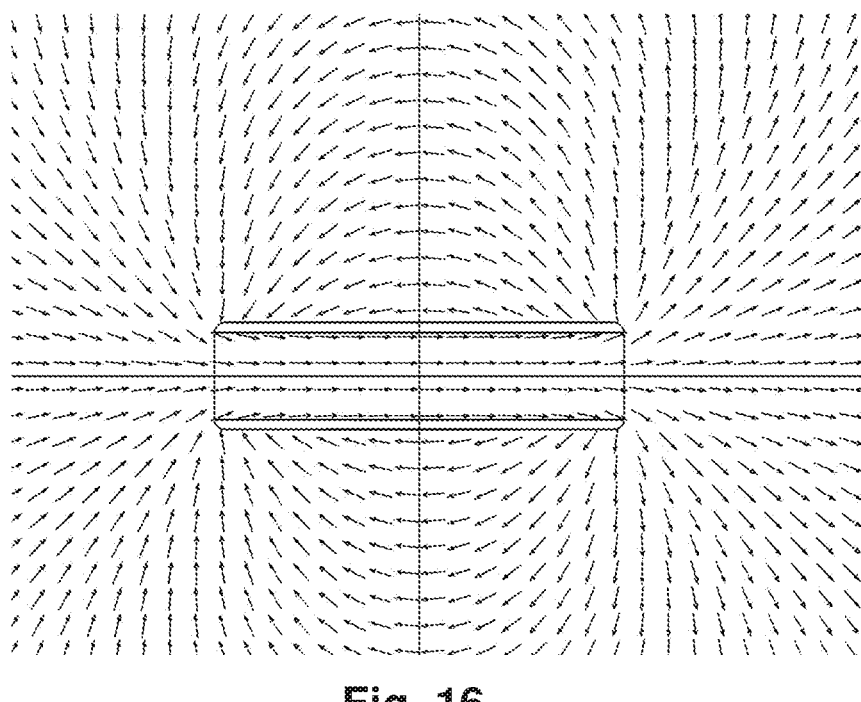

FIG. 16 illustrates the direction of the magnetic flux generated by an ordinary implant magnet that is homogeneously magnetized.

FIG. 17 illustrates the direction of the magnetic flux generated by an implant magnet having north and south end portions having individual magnetic dipole moments that are inclined with respect to the overall magnetic dipole moment of the implant magnet according to an embodiment of the present invention.

Figure 18:
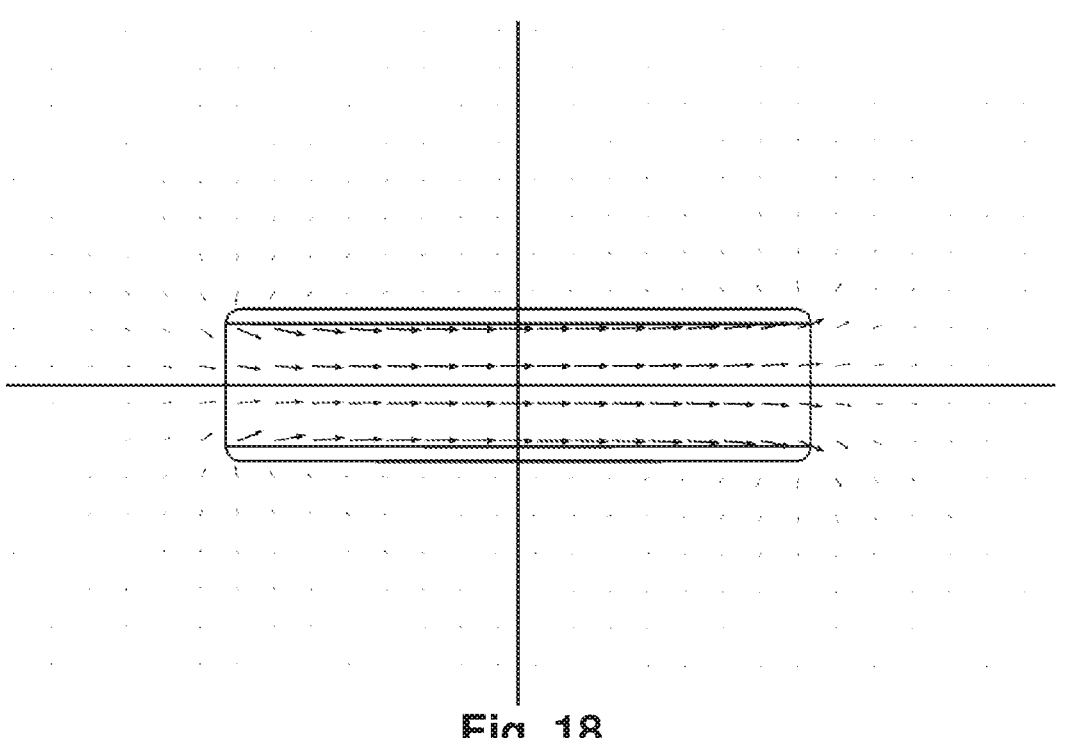

FIG. 18 illustrates the flux density of the ordinary implant magnet of FIG. 16.

Figure 19:
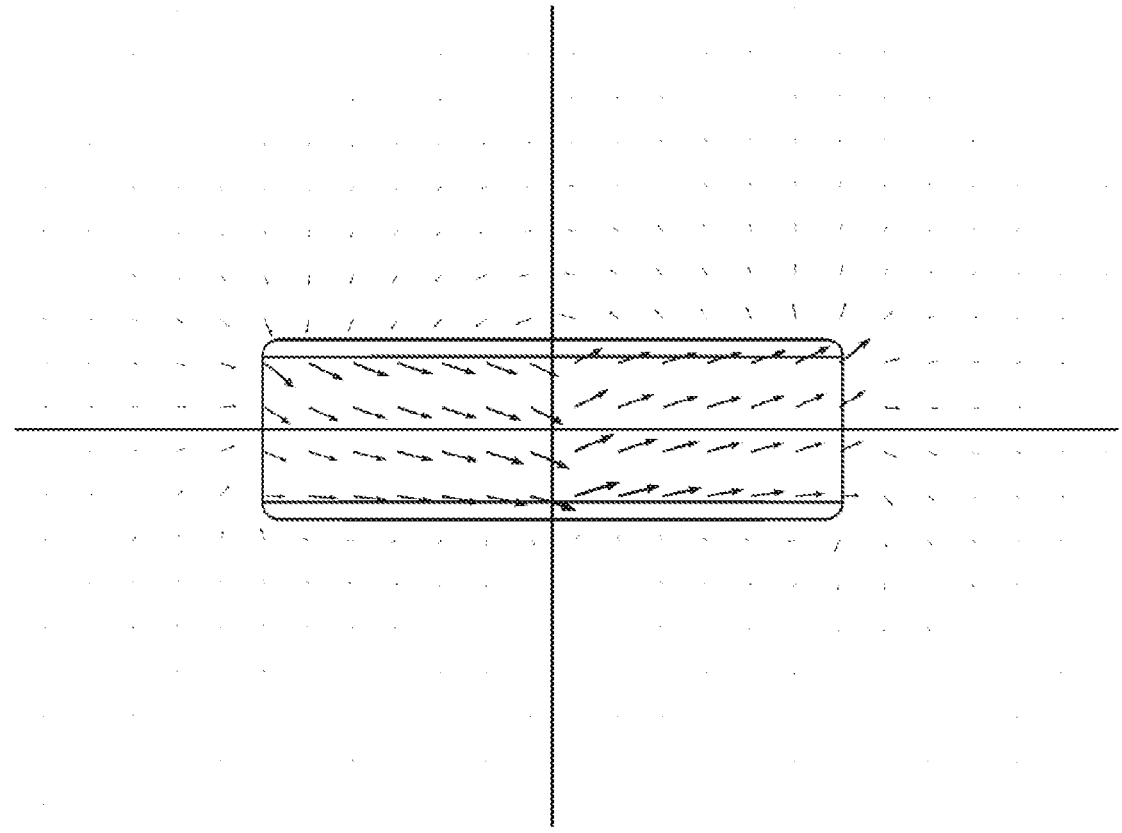

FIG. 19 illustrates the flux density of the implant magnet of FIG. 17 according to an embodiment of the present invention.

Figure 20:
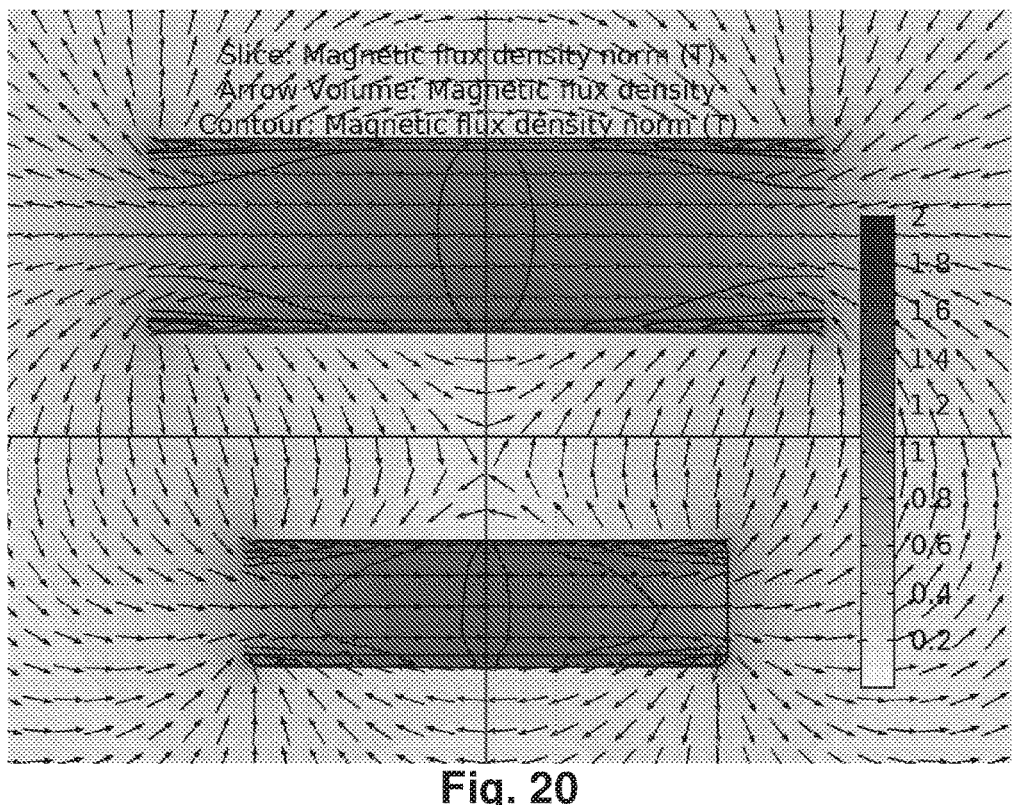

FIG. 20 shows the magnetic flux density generated upon the interaction of a homogeneously magnetized external magnet and the ordinary implant magnet of FIG. 16.

Figure 21:
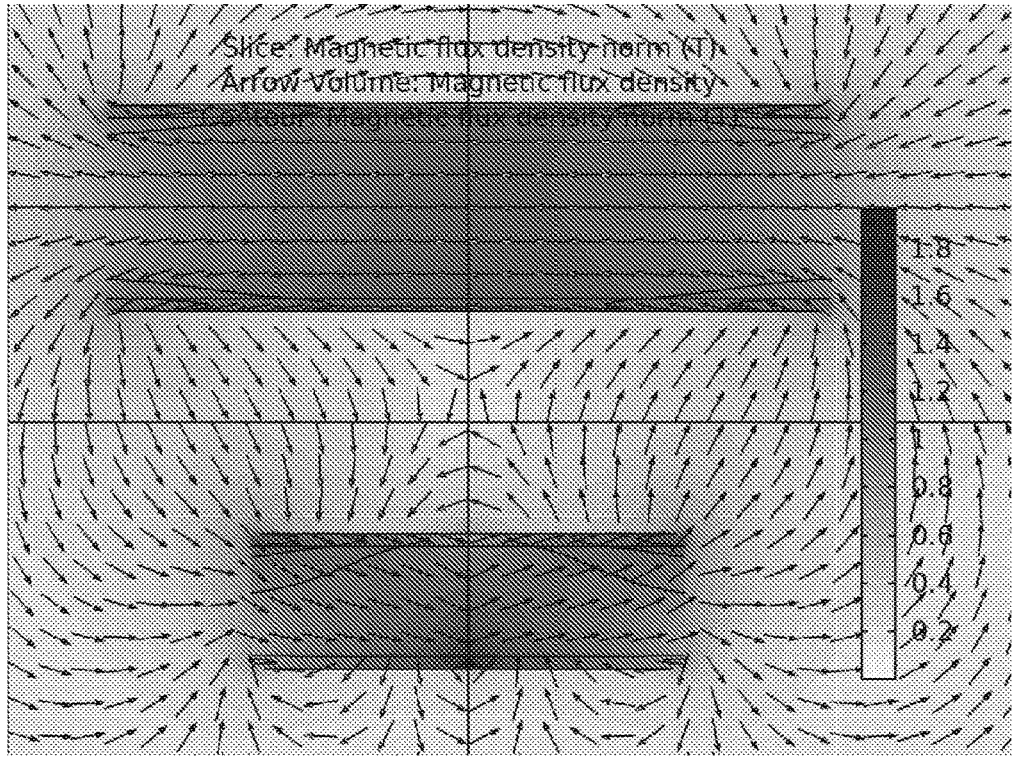

FIG. 21 shows the magnetic flux density generated upon the interaction of homogeneously magnetized external magnet and the implant magnet of FIG. 17 according to an embodiment of the present invention.

Figure 22:
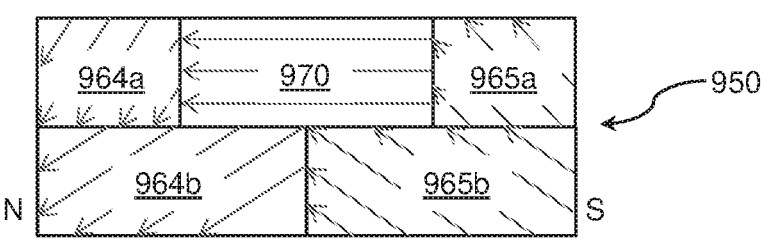
Figure 22:
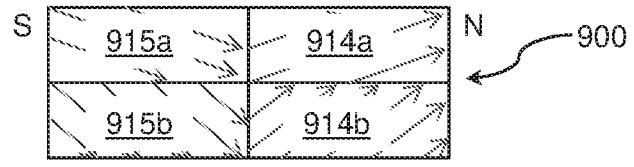

FIG. 22 is a schematic sectional view of an implant magnet and an external magnet according to a further embodiment of the invention.

Figure 23:
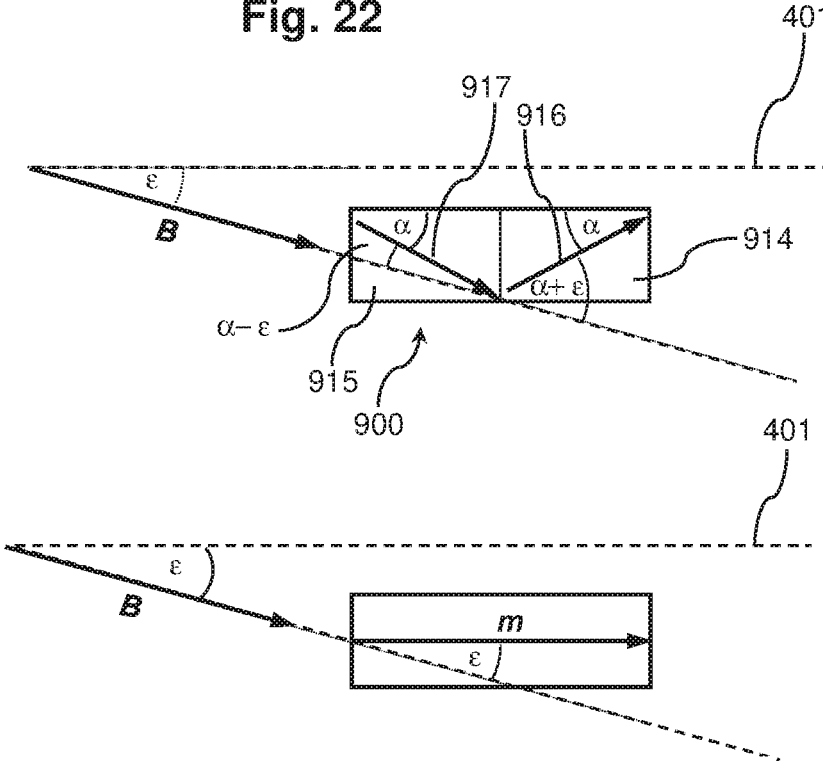

FIG. 23 is a schematic view illustrating the torque applied by an external magnetic field to a conventional implant magnet and an implant magnet according to an embodiment of the present invention.

DETAILED DESCRIPTION OF SPECIFIC EMBODIMENTS

A larger distance between the two magnetic poles has the advantage that the attractive magnetic force for an external magnet does not decrease so steeply with increasing distance between the magnets. Embodiments of the present invention are directed to an improved implant magnet arrangement that uses two cylindrical implant magnets with magnetization direction having a V-shaped magnetic angle. These magnets are mounted in the implant device such that a "strong" side (i.e. the side with high magnetic flux) faces at least partly towards the overlying skin. Both magnets are mounted inside a magnet case in which they can turn also around the rotation axis of the case.

Figure 1:
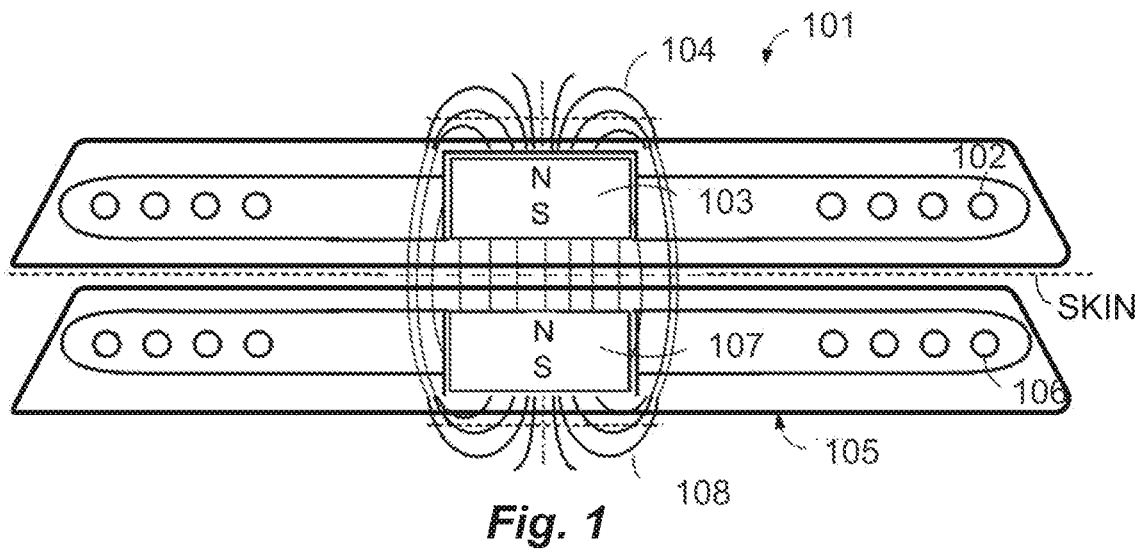
FIG. 1 shows portions of a typical cochlear implant system and the magnetic interaction between the implant magnet and the external implant magnet.
Figure 2:
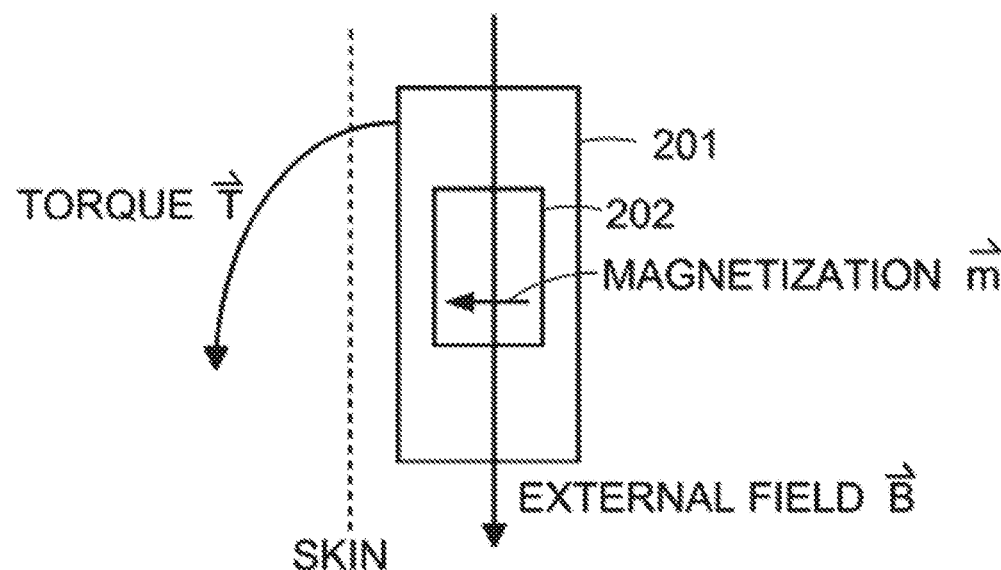
FIG. 2 illustrates the force interactions that can occur between an implant magnet and the applied external magnetic field for an MRI system.
Figure 3A:
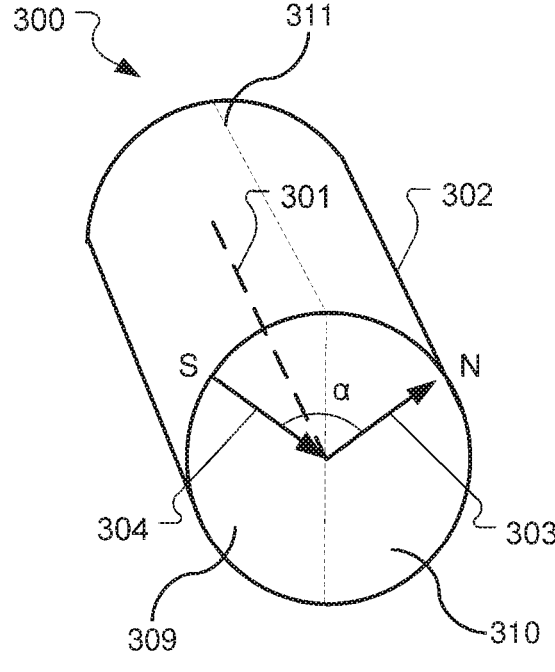
FIG. 3A shows an example of a cylindrical implant magnet with a V-shaped magnetic angle according to an embodiment of the present invention.
Figure 3B:
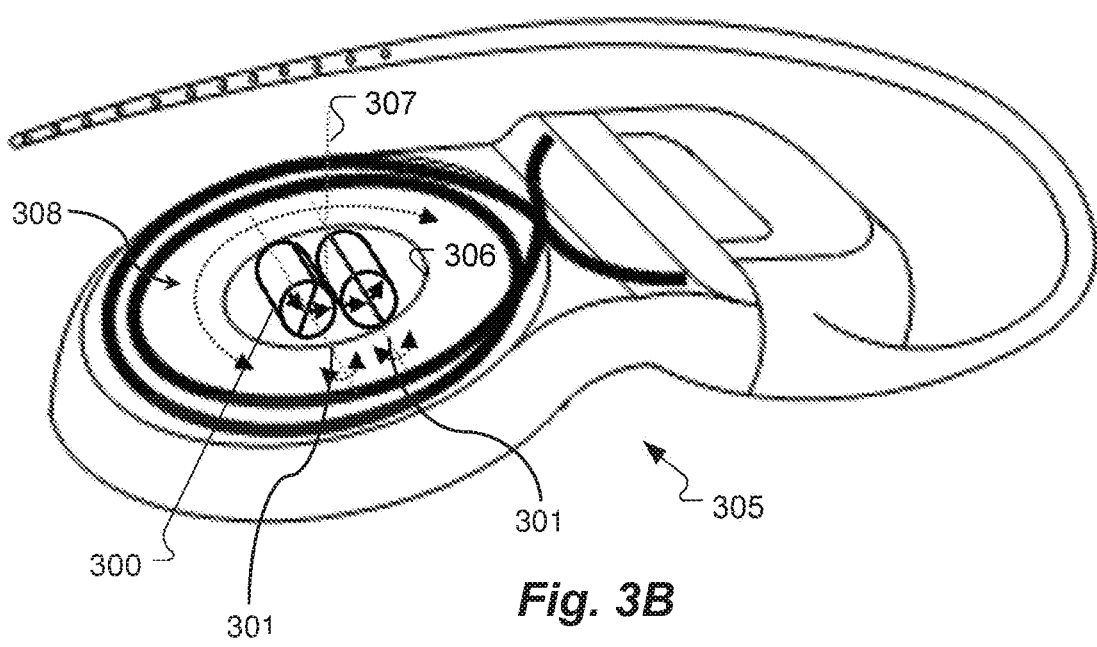
FIG. 3B shows an example of a cochlear implant device with two implant magnets of the type shown in FIG. 3A.

FIG. 3A shows an example of a cylindrical implant magnet 300 with a V-shaped magnetic angle α according to an embodiment of the present invention, and FIG. 3B shows an example of a cochlear implant device 305 with two implant magnets 300 of the type shown in FIG. 3A. The cochlear implant device 305 contains signal processing circuitry (not shown) configured for receiving an implant communications signal transmitted from an external transmitting coil through overlying skin of an implanted patient, and an outermost surface 308 adapted to lie between the overlying skin and underlying skull bone of the implanted patient.

There is a magnet case 306 within the implant device 305 with a case rotation axis 307 that is perpendicular to the outermost surface 308 of the implant device 305. The magnet case 306 is configured to be rotatable about the case rotation axis 307. Typically, the magnet case 306 is surrounded by a receiver coil of the implant device 305. The magnet case 306 may be metallic (e.g. made of titanium), or it may be made of a biocompatible non-metallic material (e.g. PEEK, FEP, PTFE, PSU, etc.) and may be coated (e.g. with Parylene). The magnet case 306 may be adapted to facilitate long-term hermetic encapsulation, and/or it may be adapted to be surgically removable for minimized susceptibility to MRI artefacts.

An implant magnet arrangement includes one or a plurality of cylindrical magnets 300 located within the magnet case 306 and configured to cooperate with a corresponding external holding magnet in an external device located over the overlying skin to magnetically hold the external device against the overlying skin. Each cylindrical implant magnet 300 has a center cylinder axis 301 that is perpendicular to the case rotation axis 307, and each cylindrical magnet 300 is configured to be rotatable about its center cylinder axis 301.

Each cylindrical magnet 300 has an outer cylindrical surface 302 with a north magnetic pole and a south magnetic pole. In the most general sense, a "cylindrical surface" is a surface consisting of all the points on all the lines which are parallel to a reference line and which pass through a fixed plane curve in a plane not parallel to the given line. In the present disclosure, the cylinder is a so-called right circular cylinder, in which the "fixed plane curve" is a circle, and the reference line is a line that is perpendicular to circle plane, for example the center cylinder axis 301. A north magnetic direction 303 is defined by a radial vector extending from the center cylinder axis 301 to the north magnetic pole. And a similar south magnetic direction 304 is defined by a radial vector extending from the south magnetic pole to the center cylinder axis 301. The north magnetic pole and the south magnetic pole are arranged with respect to each other so as not to lie on a common diameter through the center cylinder axis 301 such that the north magnetic direction 303 and the south magnetic direction 304 form a "magnetic angle" a that is less than 180 degrees with a vertex at the center cylinder axis 301. For example, the magnetic angle $\alpha$ may specifically be between 90° and 140° (or some other defined range). Such magnetic angle $\alpha$ can be established for example by forming the cylindrical magnet 300 from two preformed portions 309 and 310 which are magnetized according to the above-mentioned north and south magnetic directions 303, 304 in a manner that will be explained with reference to a further embodiment in more detail below. In the embodiment shown in FIG. 3, the preformed portions 309, 310 each correspond to a longitudinal half of the full cylindrical magnet 300 which are attached to each other along an interface indicated by the dashed line 311 in FIG. 3A.

Figure 4A:
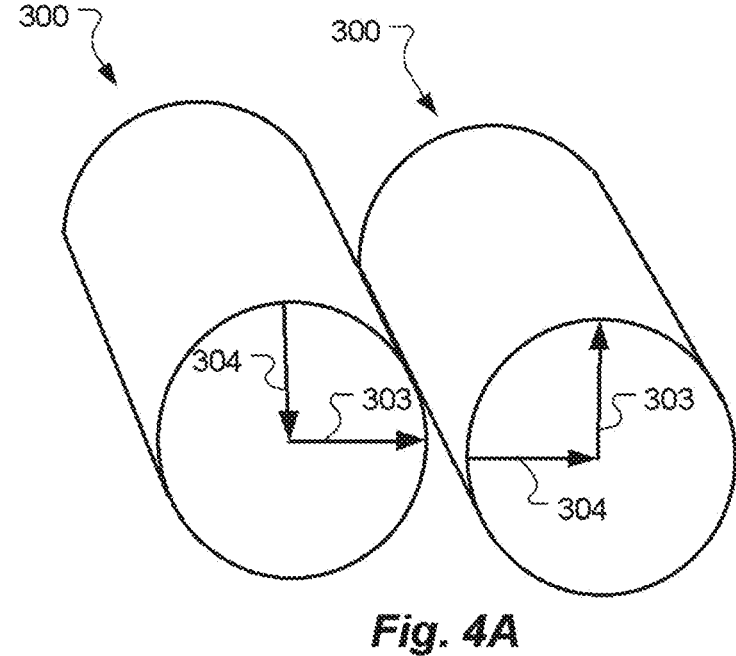
FIGS. 4A and 4B show how the magnetic fields of the implant magnets align to cooperate with an external holding magnet.
Figure 4B:
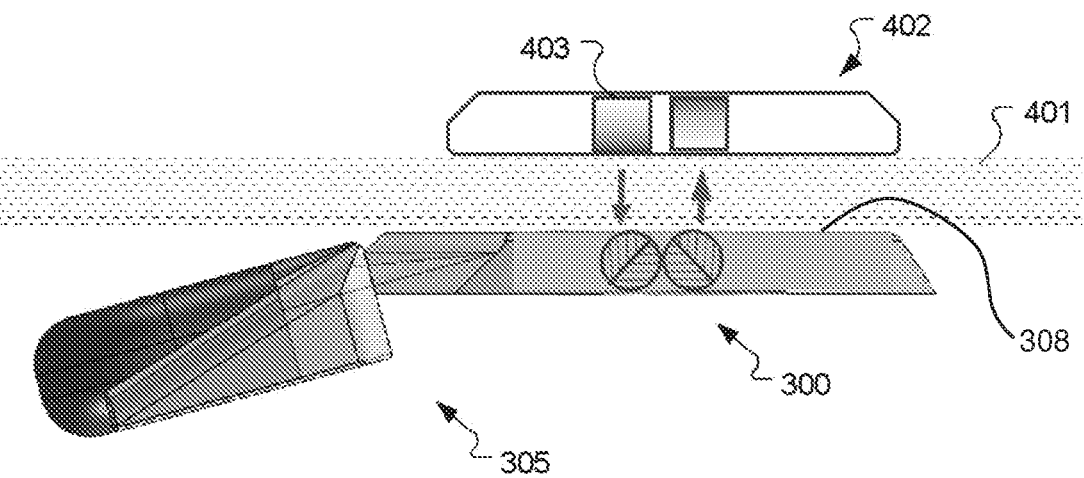

FIGS. 4A and 4B show how the magnetic fields of the cylindrical magnets 300 align to cooperate with one or more external holding magnets 403 in an external device 402 where the cylindrical magnets 300 magnetically align with respect to each other to create a common line of magnetic flux through the magnets, the magnet case, and the overlying skin to cooperate with the external holding magnet 403. Since the two cylindrical magnets 300 are arranged closely together (e.g., less than 2 mm between their outer cylindrical surfaces 302), the two adjacent magnetic poles form an attractive magnetic connection with a common magnetic direction that is parallel to the outer surface 308 of the implant device 305 and the overlying skin 401. Due to the V-shaped magnetic angle, the magnetic direction of the non-adjacent halves of the two cylindrical magnets 300 guides the magnetic flux towards the outer surface 308 of the implant device 305 and the overlying skin 401, thereby allowing a strong magnetic attraction with the external holding magnet 403 that is almost as strong as with older-type axially magnetized implant magnets that have a magnetization direction that is also normal to the skin 401.

Figure 5A:
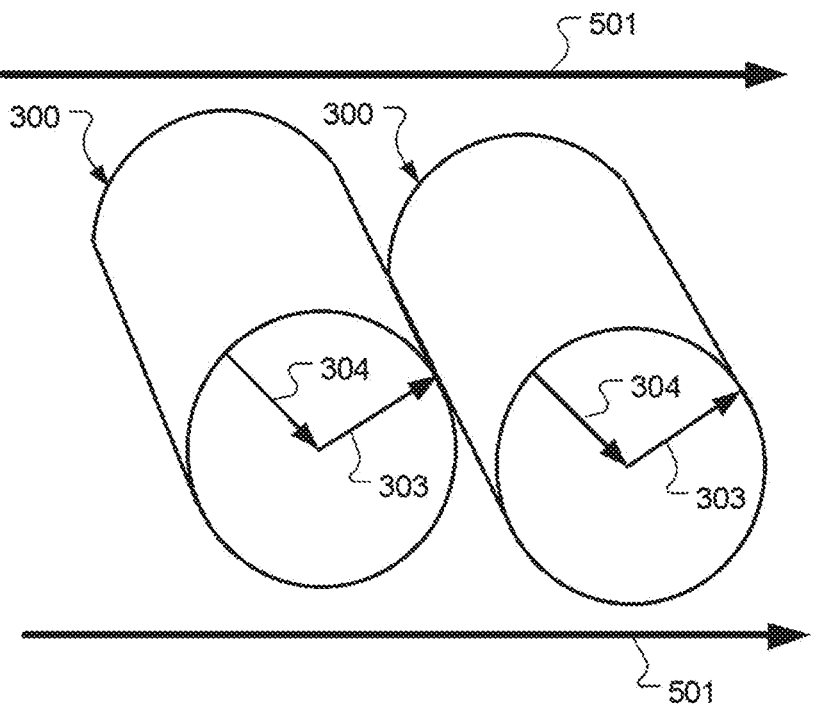
FIGS. 5A and 5B show how the magnetic fields of the implant magnets align in the presence of an MRI magnetic field.
Figure 5B:
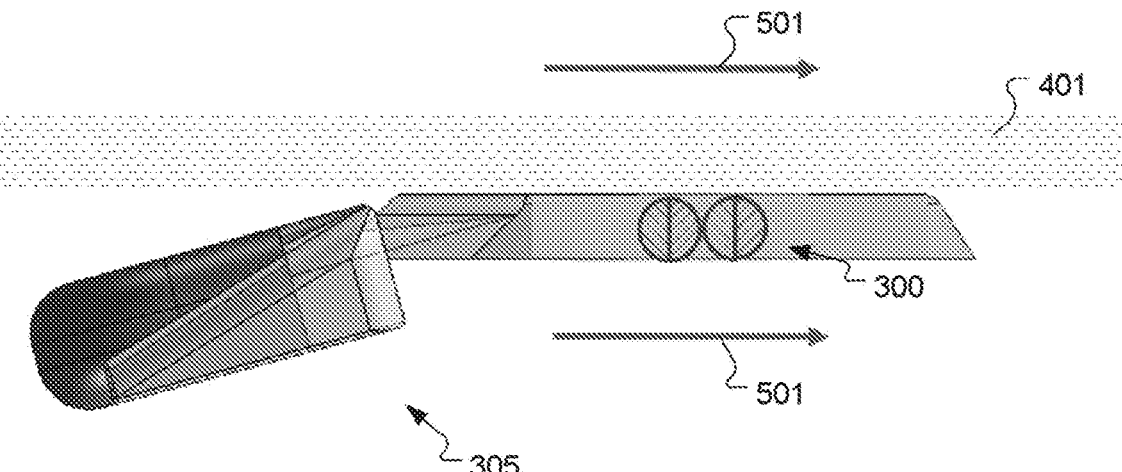

FIGS. 5A and 5B show how the cylindrical magnets 300 align in the presence of an MRI magnetic field 501. As can be seen, the two cylindrical magnets 300 immediately align relative to the external magnetic field 501 so that the torque generated by the respective magnetizations of the different halves of each magnet 300 interacting with the external magnetic field 501 cancels out. In FIG. 5B to 7B, the magnetization is schematically represented by the hatched lines.

Figure 6A:
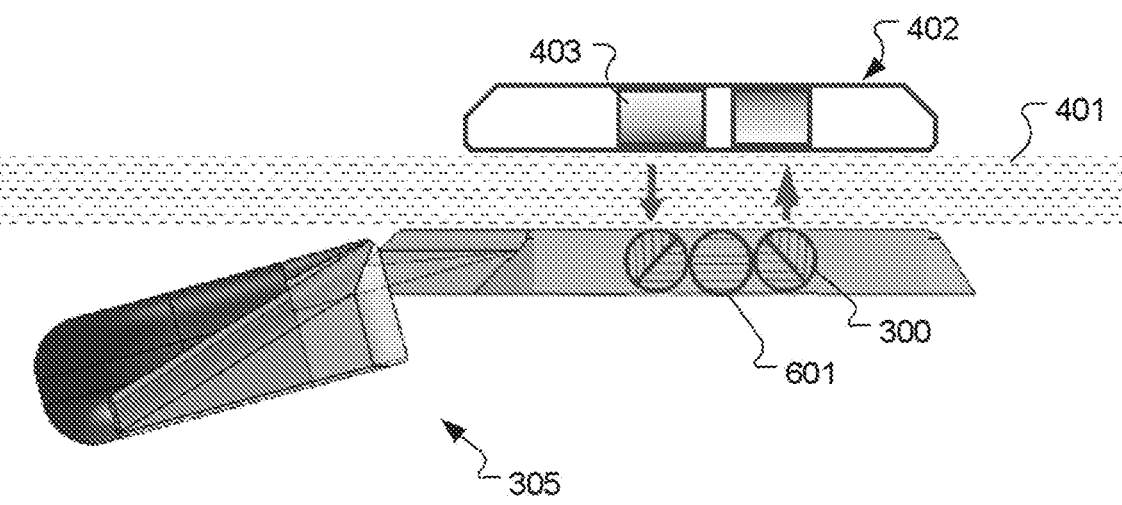
FIGS. 6A and 6B show an example of an embodiment with a diametrically magnetized supplemental cylindrical magnet located between the cylindrical magnets.
Figure 6B:
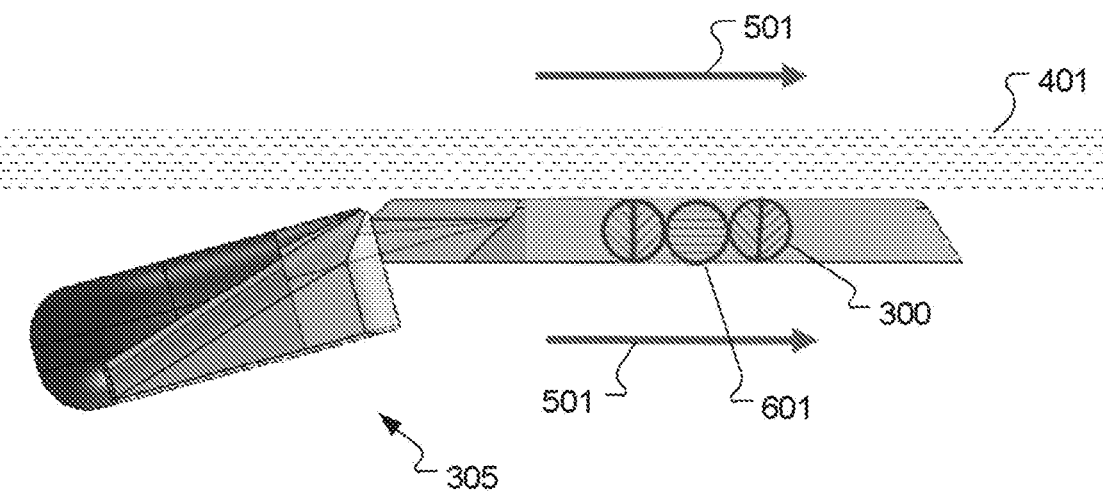

FIGS. 6A and 6B show an example of an embodiment with a diametrically magnetized supplemental cylindrical magnet 601 that is located between the cylindrical magnets 300. The supplemental cylindrical magnet 601 is configured to couple the common line of magnetic flux between the cylindrical magnets 300. This provides an increased distance between the two local maxima of the magnetic flux through the skin 401 thus improving the magnetic attraction to the external magnet 403.

Figure 7A:
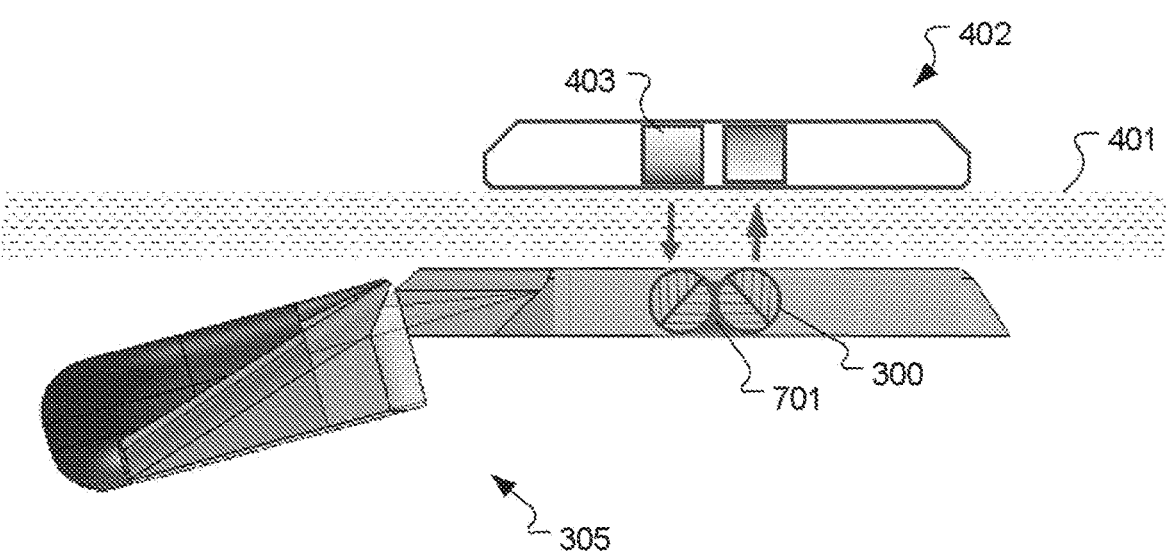
FIGS. 7A and 7B show an example of an embodiment with soft magnetic material located between the cylindrical magnets.
Figure 7B:
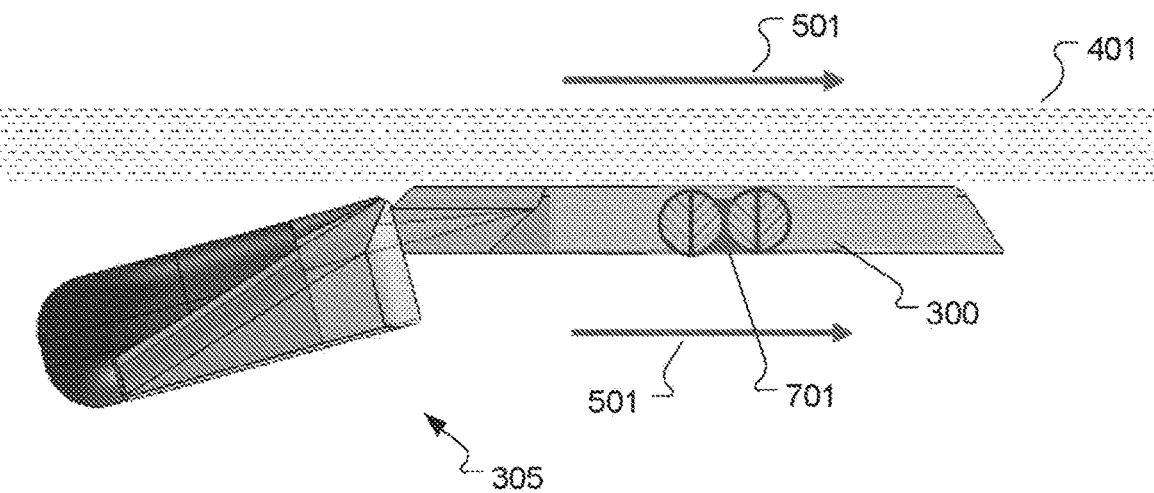

FIGS. 7A and 7B show an example of an embodiment with soft magnetic material 701 that is located between the cylindrical magnets 300 to couple the common line of magnetic flux between the cylindrical magnets 300.

In the embodiments described above, the cylindrical magnets 300 are configured to be fully rotatable about the center cylinder axis 301 through a complete rotation range of 360 degrees, and so that the magnet case 306 containing the cylindrical magnets 300 can turn around its case axis 307. Otherwise, when the center cylinder axis 301 were fixed and a strong external magnetic field 501 is oriented anti-parallel to the cylindrical magnets 300, the magnets would flip by 180° and the magnetically-strong side of the magnets would then face towards the underlying skull in a medial direction instead of towards the skin in lateral direction. Note that the orientation of the external magnetic field 501 in a given MRI scanner is different when an implant user is scanned with the head first versus with legs first. Accordingly, it is advantageous if the magnet arrangement can handle both of these orientations of the external magnetic field 501. Moreover, there is no general convention of the orientation of the external magnetic field 501 in MRI scanners, and in some cases where two MRI scanners are arranged next to each other in the same facility, the orientations of the respective external magnetic fields 501 are even deliberately chosen to be of opposite orientation.

Figure 8:
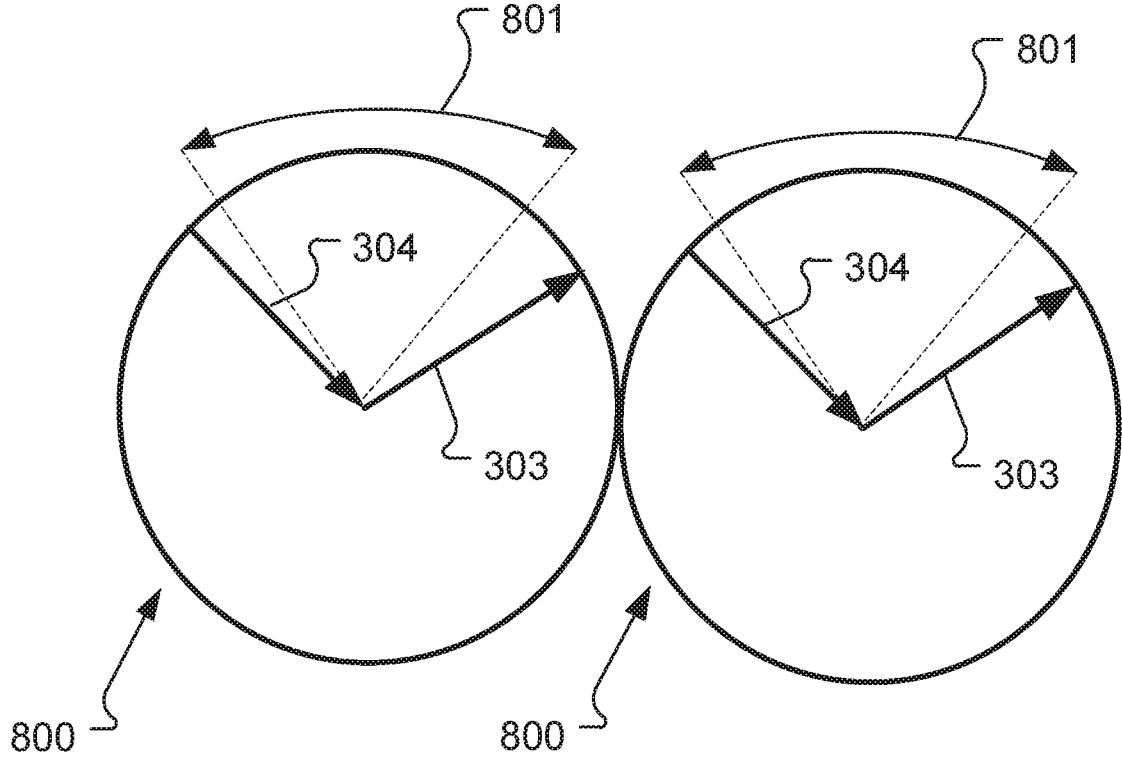
FIG. 8 shows an embodiment of cylindrical implant magnets that are configured to be limitedly rotatable through a limited rotation range according to an embodiment of the present invention.

Still, a further design variant with two cylindrical magnets in V-shaped magnetization also works when the magnets have only one degree of freedom and have a rotation angle limited to about 90° only. FIG. 8 shows an embodiment of cylindrical implant magnets 800 that are configured to be limitedly rotatable through a limited rotation range 801 of less than 180 degrees according to another embodiment of the present invention. For example, the cylindrical implant magnets may have a V-shaped magnetization with a magnetic angle between 100° and 140°, and the limited rotation range 801 may be 90°.

Figure 9A:
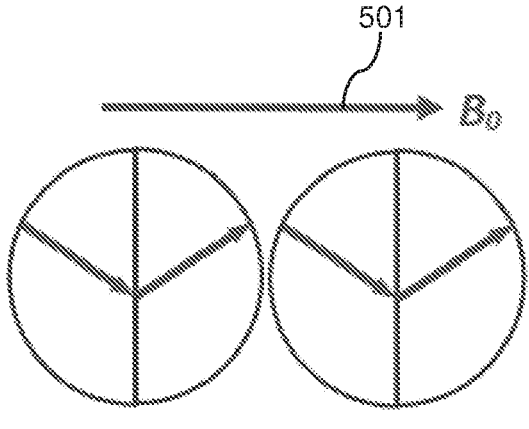
FIGS. 9A-9C show orientations of the cylindrical implant magnets for different orientations of an external MRI magnetic field.
Figure 9B:
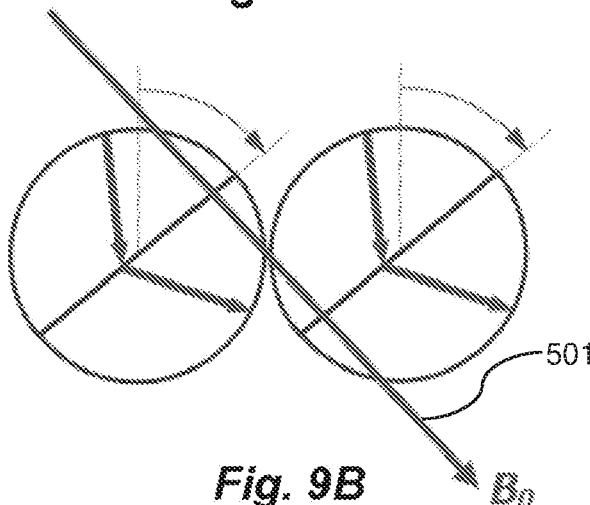
Figure 9C:
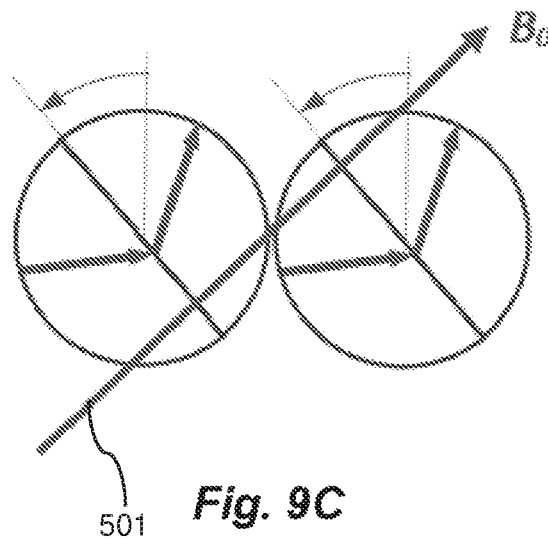

FIGS. 9A-9C show orientations of the limited rotation range cylindrical implant magnets 800 for different orientations of an external MRI magnetic field 501. As long as the strong external magnetic field 501 has a component oriented parallel to the overall magnetization of the cylindrical implant magnets 800, the magnets behave the same as with the other embodiments described above.

Figure 10A:
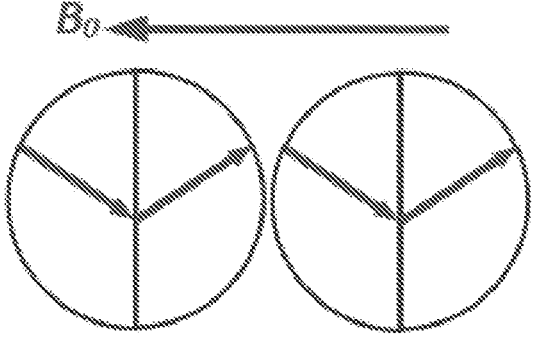
FIGS. 10A-10C show orientations of the cylindrical implant magnets for reverse magnetization m a reduced rotatability embodiment of the present invention.
Figure 10B:
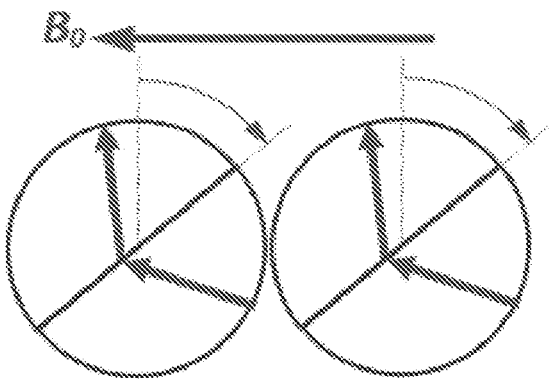
Figure 10C:
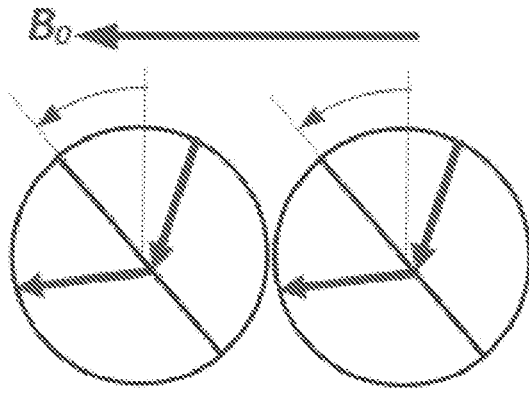

FIGS. 10A-10C show orientation of the limited range cylindrical implant magnets for reverse magnetization m a reduced rotatability embodiment of the present invention. When a strong external magnetic field is oriented antiparallel to the overall magnetization of the cylindrical implant magnets 800, they cannot turn by roughly 180° to align to be parallel with the external magnetic field. Instead, each implant magnet 800 reverses its magnet polarity.

In the embodiments described above, despite some individual parts of the implant magnet being oriented perpendicular to the skin surface, the magnets do not weaken in an MRI environment because they immediately turn into a safe orientation relative to the strong static magnetic field of the MRI scanner. Each individual magnet always has a component parallel to the strong static magnetic field of the MRI scanner. And so each individual magnet always aligns such that there is no torque to the outside. The magnetic flux is directed to the skin side and reduced in medial direction. Therefore, the MRI artefact reaches less into the medial direction and is more oriented towards the skin side.

Figures 11, 12, 13:
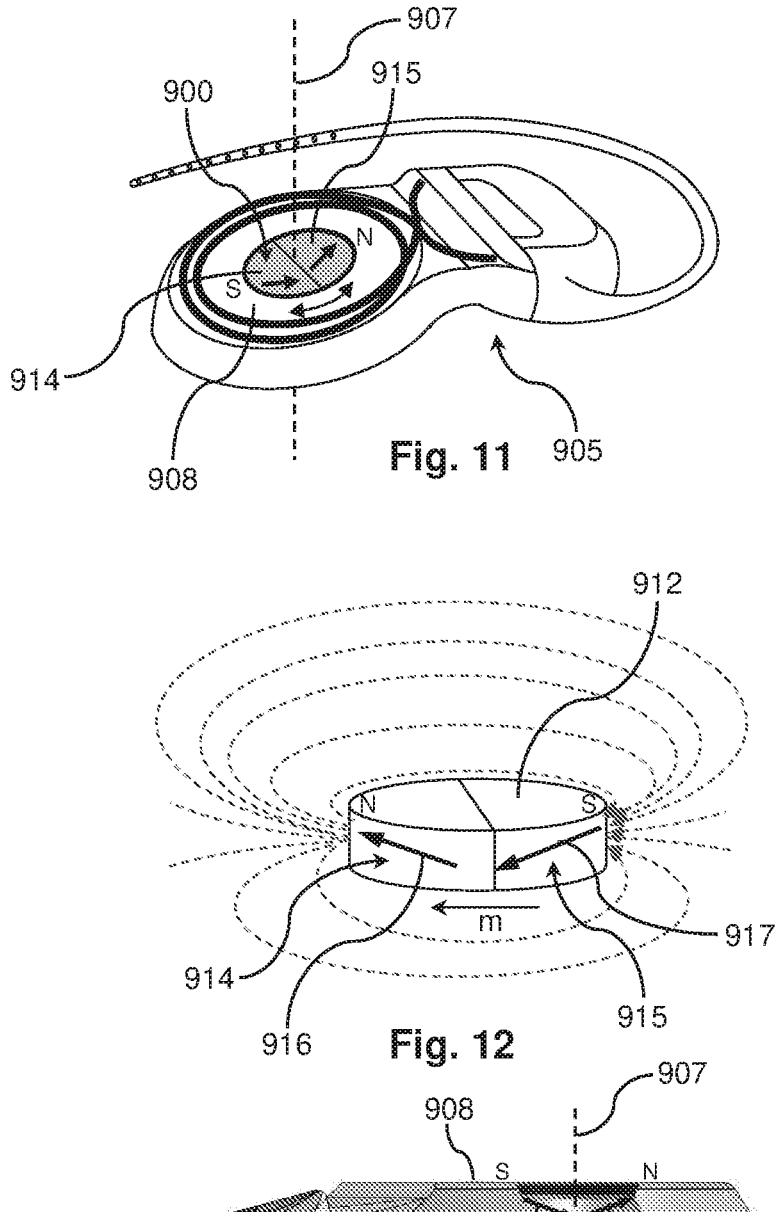
FIG. 11 shows a further example of a cochlear implant device using an implant magnet with north and south end portions having individual magnetic dipole moments that are inclined with respect to the overall magnetic at the moment of the implant magnet.
FIG. 12 is a perspective view of an implant magnet of the type used in the device of FIG. 11.
FIG. 13 is a side view of the device of FIG. 11.

Shown in FIG. 11 is an example of a further implant device, in the specific embodiment a cochlear implant device 905 that is generally similar to the cochlear implant device 305 of FIG. 3B. The cochlear implant device 905 contains signal processing circuitry (not shown) configured for receiving an implant communications signal transmitted from an external device, such as an external device as shown under reference sign 402 in FIGS. 4B and 6A through overlying skin 401 of an implanted patient.

The implant device 905 includes an outermost surface 908 adapted to lie between the overlying skin 401 and underlying skull bone and is at least approximately parallel to the skin 401 of the implanted patient. The implant device 905 further comprises an implant magnet 900 configured to cooperate with an external holding magnet in an external device 402 to be located over the overlying skin 401 to magnetically hold the external device against the overlying skin 401.

As indicated in FIG. 11 to 13, the implant magnet 900 has a north magnetic pole, a south magnetic pole, and as a whole has an overall magnetic dipole moment m that is parallel to the outermost surface 908 and hence parallel to the skin 401 (not shown in FIG. 11 to 13). The overall magnetic dipole moment m need not be precisely parallel to the outermost surface 908 (the skin 401), but should be at least approximately parallel to it, for example form an angle of 30° or less, preferably 20° or less with respect to said outermost surface 908.

The implant magnet 900 is rotatable around a rotation axis 907 that in the embodiment shown is perpendicular to said outermost surface 908 so that in each available rotational position of said implant magnet 900 upon rotation around its rotation axis 907, the overall magnetic dipole moment m is parallel to said outermost surface 908.

As is seen in FIGS. 12 and 13, the implant magnet 900 has an outer end surface 912 facing said outermost surface 908 of said implant device 905 (i.e. towards the skin 401 in the implanted state), and an inner end surface 913 facing away from said outermost surface 908 (i.e. towards the inside of a patient head in the implanted state). Both of the outer and inner end faces 912, 913 are planar surfaces and are perpendicular to said rotation axis 907. For example, the implant magnet 900 may have a cylindrical disc shape, in which the side face is formed by a cylindrical surface, as shown in FIG. 12. However, the side face need not be precisely cylindrical, but could have a slightly conical shape, as shown in FIG. 13. It is however preferred that said implant magnet 900 has a shape that is rotationally symmetric around said rotation axis 907.

Moreover, the implant magnet 900 has a north end portion 914 including said north magnetic pole and a south end portion 915 including said south magnetic pole. Both of said north and south end portions 914, 915 are formed from permanent magnetic material and each have an individual magnetic dipole moment 916, 917 that is inclined with respect to said overall magnetic dipole moment m, as will be explained in more detail with reference to FIG. 14.

FIG. 14 again schematically shows an implant device 905 in a sectional view including an implant magnet 900, as well as an external device 955 comprising an external magnet 950. By magnetic interaction between the internal and external magnets 905, 950, the external device 955 may be attached to the skin 401 of a patient. The internal magnet 900 is comprised of two halves, one being formed by the north end portion 914 and the other by the south end portion 915. The hatched lines with arrowheads indicate the local magnetization M. It is seen that the local magnetizations in the north and south end portions 914, 915 have deviating directions, thereby leading to what was referred to as the "magnetic angle" with reference to the first embodiment of the invention above. Each of the north and south end portions 914, 915 has an individual magnetic dipole moment 916, 917, which corresponds to the space integral over the magnetization M in the respective portion. It is then seen that although the overall dipole moment m of the implant magnet 900 as a whole is directed parallel to the outermost surface 908 of the implant device 905, each of the individual magnetic dipole moments 916, 917 are inclined with respect to the overall dipole moment m.

More precisely, it is seen that the magnetic dipole moment 916 in said north end portion 914 is inclined in a plane perpendicular to the outermost surface 908/skin 401, to have a component pointing towards said outermost surface 908, and said individual magnetic dipole moment in said south end portion 915 is inclined to have a component pointing away from said outermost surface. This leads to a situation where the bigger part of the magnetic flux B generated by said implant magnet 901 is located to the outside, where it is needed for generating a holding force holding the external magnet 950.

In particular, in preferred embodiments, when simply regarding the internal magnet 900 in isolation, i.e. without presence of the external magnet 950 and when placed in air or vacuum, at least 55%, preferably at least 65% or even 70% or more of the total magnetic flux B of a magnetic field generated outside of the implant magnet 900 is located "outside" of a middle plane arranged at equal distances from the outer and inner end surfaces 912, 913. Herein, "outside of the middle plane" means the side at which said outermost surface 908 is located in the assembled state. This way, the holding force can be significantly increased over and implant magnet of the same size and material which would be homogeneously magnetized parallel to the skin 401.

Figure 14:
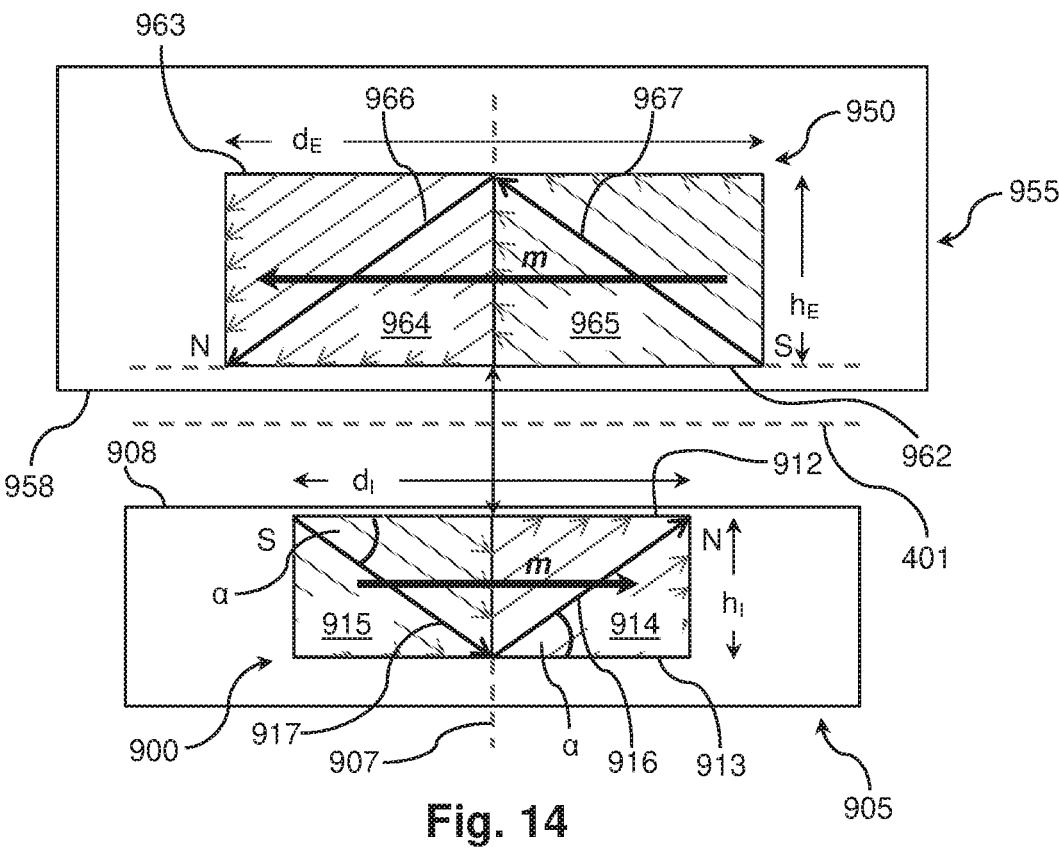
FIG. 14 is a schematic sectional view showing an implant device and an external device with corresponding magnets.

In the embodiment of FIG. 14, the implant magnet 900 has a diameter $d_I$ in a direction parallel to the overall magnetic dipole moment and a thickness $h_I$ in a direction perpendicular to said outermost surface. In view of this geometry, in both of said north and south end portions 914, 915, said individual magnetic dipole moment 916, 917 is inclined with respect to said overall magnetic dipole moment m by an angle $\alpha=\arctan(h_I/(d_I/2))$. Herein, the angle $\alpha$ is measured with respect to a plane that is parallel to the outermost surface 908. This choice for the angle $\alpha$ is large enough for providing a significant improvement in attraction force with the external magnet 950 over a prior art implant magnet of same size and material that would be homogeneously magnetized parallel to the skin 401. A significantly larger angle $\alpha$ has been found to be less favorable, for two reasons. First, for larger angles $\alpha$, the distance between the north and south poles would decrease, which in turn would lead to an excessive decrease in holding force with increasing distance from the implant magnet 900. Secondly, the angle α of inclination between each individual magnetic dipole moment 916, 917 in said north and south end portions 914 and 915 with respect to the overall magnetic dipole moment m should generally be no more than 60°, and with a certain safety margin, preferably no more than 50°, such as to avoid a situation in which the implant magnet 900 could be inadvertently weakened or demagnetized in a strong external MRI field in case the patient does not hold his or her head straight during the MRI procedure, but for example tilted to one side by e.g. up to 30°. Preferred ranges for the angle α are arctan $(h_z/(d_z/2))-15°\leq\alpha\leq$arctan $(h_z/(d_z/2))+7°$, more preferably arctan $(h_z/(d_z/2))-10°\leq\alpha\leq$arctan $(h_z/(d_z/2))+5°$, provided that in each case, preferably $\alpha\leq50°$.

Note that the external magnet 950 in the external device 955 of the embodiment of FIG. 14 has a similar structure than the internal magnet 905. That is to say, the external magnet 950 has an overall magnetic dipole moment m that is parallel to the innermost surface 958 of the external device 955 that lies adjacent to the skin 401. The external magnet 950 likewise has a north end portion 964 and a south end portion 965 in which the respective individual magnetic dipole moment 966, 967 is inclined with respect to the overall dipole moment m, such that the individual magnetic dipole moment 966 in said north end portion 964 has a component pointing towards the innermost surface 958 of the external device 955, and such that the individual magnetic dipole moment 967 in said south end portion 965 has a component pointing away from said innermost surface 958 of the external device 955. However, while the implant magnet 905 has been specifically devised for compatibility with an MRI external magnetic field, the external device 955 can be taken off the cochlear implant user prior to the MRI procedure, such that it does not need to employ a similar design. In particular, the external magnet 950 need not be rotatable, and it is also not necessary that its overall magnetic dipole moment m is parallel to the innermost so face 958 (skin 401). Nevertheless, in preferred embodiments, the design of the external magnet 950 is similar to that of the internal magnet 905, incorporating some or all of the features that were described in the above summary of embodiments of the invention.

Figure 15:
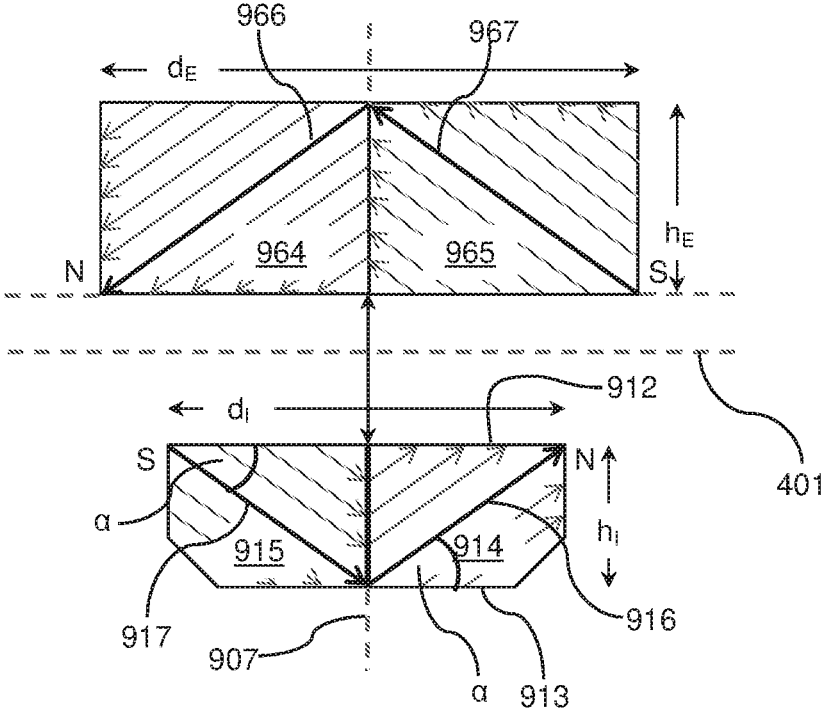
FIG. 15 is a schematic sectional view showing magnets of an implant and an external device.

FIG. 15 shows an embodiment which is similar to that of FIG. 14, with the main difference that the edges of the implant magnet 905 at the inner end surface 913 are chamfered. This allows for an improved magnetic flux, and further allows for concentrating more than half of the magnet mass towards the outside of the middle plane, i.e. on a side of said middle plane at which said outermost surface 908 is located.

FIG. 16 illustrates the direction of the magnetic flux generated by an ordinary implant magnet that is homogeneously magnetized. In contrast to this, FIG. 17 illustrates the direction of the magnetic flux generated by an implant magnet 900 of the type shown in FIG. 11 to FIG. 14 having north and south end portions 914, 915 with individual magnetic dipole moments 916, 917 that are inclined with respect to the overall magnetic dipole moment of the implant magnet 900.

FIG. 18 illustrates the flux density of the ordinary implant magnet of FIG. 16. In other words, while FIG. 16 only shows the direction of the magnetic flux, FIG. 18 indicates the flux density, which is represented by the size of the arrows displayed in the diagram. It is seen that both, the magnetic flux direction and the magnetic flux density are mirror symmetric with respect to the aforementioned middle plane of the magnet, which is a consequence of the homogeneous magnetization. FIG. 19 shows the flux density of the implant magnet 900 according to an embodiment of the invention of FIG. 17. It is seen that in the implant magnet 900 of this embodiment, the poles are shifted "upwards" in the representation of FIG. 19, such that they are located above the middle plane. Indeed, as the skilled person will appreciate, the poles correspond to the regions where the flux density at the surface of the implant magnet 900 is the highest, and these locations are found at the upper left and right corners in the representation of FIG. 19, which is hence consistent with what is schematically shown in FIGS. 14 and 15. Moreover, it is seen that of the total magnetic flux of the magnetic field generated outside the implant magnet 900 when taken in isolation, the bigger part is located above the middle plane. Accordingly, the magnetic field generated by the implant magnet 900 according to an embodiment of the invention is indeed suitable for generating higher attraction forces when cooperating with an external magnet.

FIG. 20 shows the magnetic flux density generated upon the interaction of a homogeneously magnetized external magnet and the ordinary implant magnet of FIGS. 16 and 18. For comparison, FIG. 21 shows the magnetic flux density generated upon the interaction of the same homogeneously magnetized external magnet as in FIG. 20 and the implant magnet 900 of FIGS. 17 and 19. It is seen that using the implant magnet 900 according to an embodiment of the invention, the attraction force per unit volume of the implant magnet 900 could be increased by 15%. This gain in attraction force can be even increased further if an external magnet of the type shown under reference sign 950 in FIGS. 14 and 15 is used.

In the embodiment shown, both the implant magnet 900 and the external magnet 950 are manufactured from two separate anisotropic magnet pieces which form the north and south end portions 914, 915; 964, 965 in the finished magnet 900, 950. The anisotropic magnet pieces each have a preferred magnetization direction that corresponds to the direction of the individual magnetic dipole moment 916, 917; 966, 967 in the finished magnet 900, 950. The preferred magnetization direction can be imprinted on the magnet material by applying a corresponding magnetic field upon its manufacture, for example during a corresponding sintering process. The respective magnet pieces can be joined for example by gluing them together, and only after joining them, the final magnetization is established by applying a strong magnetization pulse parallel to the direction of the overall dipole moment of the finished magnet 900, 950. Due to the anisotropic character of the magnet pieces, this magnetization pulse will not magnetize both pieces along the direction of the magnetic field of the strong magnetization pulse, but will magnetize them according to their preferred magnetization directions. In preferred embodiments, the implant magnet 900 and/or the external magnet 950 is a rare earth magnet, in particular a rare earth magnet comprising neodymium, samarium, terbium, dysprosium or holmium.

In the embodiments of both, FIG. 14 in FIG. 15, the north and south end portions 914, 915; 964, 965 are directly adjacent with each other, each forming one of two halves of the implant magnet 900 and external magnet 950, respectively.

In alternative embodiments, however, north and south end portions of said implant magnet may be separated from each other by an intermediate portion having an individual magnetic dipole moment that is (at least approximately) parallel to said overall magnetic dipole moment. An example for this is shown with respect to the external magnet 950 in FIG. 22, where such intermediate portion is shown at reference sign 970. This intermediate portion 970 allows for comparatively large inclinations of the magnetization in the north and south end portions 964, 965 while at the same time avoiding magnetic short-circuits at the outer surface, thereby leading to very good holding forces.

In addition or alternatively, one or both of said north and south end portions 914, 915 of said implant magnet 900 may have an outer section 914a, 915a closer to the outermost surface 908 (not shown in FIG. 22, see FIG. 14) and an inner section 914b, 915b further away from said outermost surface 908, and an angle of inclination of the individual magnetic dipole moment (indicated by the magnetization in FIG. 22) with respect to the overall magnetic dipole moment in said outer section 914a, 915a is less than in said inner section 914b, 915b. This embodiment allows for an improved magnetic flux within the implant magnet 900 while avoiding the distance of the north and south poles to decrease. A similar design is likewise indicated for the external magnet 950 in FIG. 22.

FIG. 23 shows in the lower half a conventional implant magnet having a homogeneous magnetization and a dipole moment m that is parallel to the skin 401 and that is rotatable around an axis perpendicular to the skin 401. When the implanted person is placed in an external magnetic field B of an MRI apparatus, it is generally assumed that the magnetic field B is parallel to the skin 401, and under this assumption, the implant magnet can rotate such as to bring its dipole moment m in alignment with the external magnetic field B, with no torque acting on the implant magnet anymore. However, this is an idealized assumption, because the implanted magnet might not be perfectly parallel to the skin overlying the magnet, and in practice, the skin overlying the magnet will not be precisely parallel to the external magnetic field B, due to the individual anatomy of the patient and the fact that the patient may tilt his or her head sideways. Accordingly, in practice a situation as indicated in the upper part of FIG. 23 arises, in which the magnetic dipole moment m of the conventional implant magnet will be inclined with respect to the external magnetic field by an angle ε. In this situation, a torque τ is applied to the implant magnet having a magnitude $|\tau| = |m| \cdot |B| \cdot \sin(\varepsilon)$.

The upper part of FIG. 23 shows the same situation for an implant magnet 900 according to an embodiment of the invention, having north and south end portions 914, 915 forming halves of the implant magnet 900 and having respective individual magnetic dipole moments 916, 917 which are each inclined with respect to the total magnetic dipole moment of the implant magnet 900 by an angle α. This means that in each of the two halves forming the north and south end portions 914, 915, there will be a local torque applied even if the external magnetic field B is parallel to the overall magnetic dipole moment of the implant magnet 900, but these two local torques cancel each other. Assuming that the magnitude of the individual dipole moment 916, 917 in each of the north and south end portions 914, 916 is $m_0$, the magnitude of the total torque in case of an inclined external magnetic field B as illustrated in the lower part of FIG. 23 can be calculated as follows:

$$|\tau| = m_0 \cdot |B| \cdot \sin(\alpha + \varepsilon) - m_0 \cdot |B| \cdot \sin(\alpha - \varepsilon) = 2 \cdot m_0 \cdot |B| \cdot \sin(\varepsilon) \cdot \cos(\alpha).$$

Comparing this torque to the torque experienced by a conventional homogeneously magnetized implant magnet of same dimensions, one can assume that $2 \cdot m_0 \approx |m|$, with $|m|$ being again the magnitude of the magnetic dipole moment of the conventional homogeneously magnetized implant magnet. It is therefore seen that the torque experienced by the implant magnet 900 according to an embodiment of the invention in the inclined external magnetic field B is actually reduced by a factor of $\cos(\alpha)$ as compared to the conventional magnet of the same size, making the implant magnet 900 according to an embodiment of the invention less sensitive to deviations from the idealized assumption of an external magnetic field being parallel to the skin.

Although various exemplary embodiments of the invention have been disclosed, it should be apparent to those skilled in the art that various changes and modifications can be made which will achieve some of the advantages of the invention without departing from the true scope of the invention.

The invention claimed is:

1. An implant device comprising:
signal processing circuitry configured for receiving an implant communications signal transmitted from an external transmitting coil through overlying skin of a patient, wherein the implant device includes an outermost surface adapted to lie between the overlying skin and underlying skull bone of the patient;
a magnet case configured to be rotatable about a case rotation axis which is at least approximately perpendicular to the outermost surface of the implant device; and
an implant magnet arrangement within the magnet case configured to cooperate with an external holding magnet in an external device to be located over the overlying skin to magnetically hold the external device against the overlying skin;
wherein the implant magnet arrangement comprises a plurality of cylindrical magnets, each with a center cylinder axis perpendicular to the case rotation axis, and each cylindrical magnet configured to be rotatable about the center cylinder axis;
wherein each cylindrical magnet has an outer cylindrical surface with a north magnetic pole and a south magnetic pole;
wherein a north magnetic direction is defined by a radial vector extending from the center cylinder axis to the north magnetic pole;
wherein a south magnetic direction is defined by a radial vector extending from the south magnetic pole to the center cylinder axis; and
wherein, for at least two of the plurality of cylindrical magnets, the north magnetic pole and the south magnetic pole for a given cylindrical magnet are arranged with respect to each other so as not to lie on a common diameter through the center cylinder axis such that the north magnetic direction and the south magnetic direction form a magnetic angle less than 180 degrees with a vertex at the center cylinder axis.

2. The implant device according to claim 1, wherein the implant magnet arrangement is configured for the plurality of cylindrical magnets to magnetically align with respect to each other to create a common line of magnetic flux through the cylindrical magnets, the magnet case, and the overlying skin to cooperate with the external holding magnet.

3. The implant device according to claim 2, further comprising:

one or more diametrically magnetized supplemental cylindrical magnets between the plurality of cylindrical magnets configured to couple the common line of magnetic flux between the plurality of cylindrical magnets.

4. The implant device according to claim 2, further comprising:

soft magnetic material between the plurality of cylindrical magnets configured to couple the common line of magnetic flux between the plurality of cylindrical magnets.

5. The implant device according to claim 1, wherein the implant magnet arrangement is configured to respond to a strong external magnetic field by rotation of the magnet case about the case rotation axis and rotation of the cylindrical magnets about their respective center cylinder axes to minimize net torque imparted to the implant device.

6. The implant device according to claim 1, wherein the magnetic angle is between 90 degrees and 140 degrees.

7. The implant device according to claim 1, wherein each cylindrical magnet is configured to be fully rotatable about the center cylinder axis through a complete rotation range of 360 degrees.

8. The implant device according to claim 1, wherein each cylindrical magnet is configured to be limitedly rotatable about the center cylinder axis through a limited rotation range of less than 180 degrees.

9. The implant device according to claim 8, wherein the limited rotation range is 90 degrees.

10. The implant device according to claim 1, wherein the implant device is a hearing implant device.

11. The implant device according to claim 10, wherein the hearing implant device is a cochlear implant.

12. An implant system comprising:

the implant device according to claim 1;

the external device comprising signal processing circuitry configured for transmitting the implant communications signal to the implant device, the external device comprising an innermost surface adapted to lie adjacent to the skin; and the external holding magnet in the external device to be located over the overlying skin and magnetically configured to cooperate with the implant magnet arrangement of the implant device such as to hold the external device against the skin.

13. The implant system of claim 12, wherein the external holding magnet has a north magnetic pole, a south magnetic pole, and as a whole has an overall magnetic dipole moment that is parallel to or at an angle of 30° or less with respect to the innermost surface of the external device.

14. The implant system of claim 13, wherein the external holding magnet has a north end portion including the north magnetic pole and a south end portion including the south magnetic pole, the north and south end portions each being formed from permanent magnetic material and each having an individual magnetic dipole moment that is inclined with respect to the overall magnetic dipole moment of the external holding magnet, wherein the individual magnetic dipole moment in the north end portion has a component pointing towards the innermost surface of the external device, and the individual magnetic dipole moment in the south end portion has a component pointing away from the innermost surface of the external device.

15. The implant system of claim 14, wherein the north and south end portions of the external holding magnet are directly adjacent with each other, and each form one of two halves of the external holding magnet.

16. The implant system of claim 14, wherein the north and south end portions of the external holding magnet are separated from each other by an intermediate portion having an individual magnetic dipole moment that is parallel to the overall magnetic dipole moment of the external holding magnet or deviates from parallel by less than 10°.

17. The implant system of claim 14, wherein one or both of the north and south end portions of the external holding magnet have an inner section closer to the innermost surface of the external device and an outer section further away from the innermost surface of the external device, wherein an angle of inclination of the individual magnetic dipole moment with respect to the overall magnetic dipole moment in the inner section is less than in the outer section.

18. The implant system of claim 14, wherein the north and south end portions of the external holding magnet are formed from anisotropic magnet elements each having a magnetization direction, wherein the anisotropic magnet elements are joined with each other or with an intermediate portion arranged in between, wherein the magnetization directions are arranged at an angle with respect to the overall dipole moment of the external holding magnet as a whole.

19. The implant system of claim 12, wherein the external holding magnet is rotatable around a rotation axis that is perpendicular to the innermost surface of the external device or deviates from perpendicular by less than 30°, wherein in each available rotational position of the external holding magnet upon rotation around the rotation axis, the overall magnetic dipole moment is parallel to or at an angle of 30° or less with respect to the innermost surface, wherein the external holding magnet has a shape that is rotationally symmetric around its rotation axis.

20. The implant system of claim 12, wherein the external holding magnet has a planar inner end surface facing the innermost surface of the external device.

21. The implant system of claim 20, wherein the external holding magnet has an average diameter $d_E$ in a direction parallel to the overall magnetic dipole moment and an average thickness $h_E$ in a direction perpendicular to the innermost surface of the external device, wherein in one or both of the north and south end portions, the individual magnetic dipole moment is inclined with respect to the overall magnetic dipole moment by an angle $\alpha$, wherein $$\arctan(h_E/(d_E/2)) - 15° \le \alpha \le \arctan(h_E/(d_E/2)) + 7°.$$

22. The implant system of claim 12, wherein the external holding magnet has an inner end surface facing the innermost surface of the external device and an outer end surface facing away from the innermost surface of the external device, wherein a middle plane is defined to be located at equal distance from the outer and inner end surfaces of the external device, and wherein the external holding magnet fulfils one or both of the following criteria (i) and (ii):

(i) at least 55% of the total magnetic flux of a magnetic field generated outside of the external holding magnet when placed in isolation in air or a vacuum is located on a side of the middle plane at which the innermost surface of the external device is located in the assembled state, (ii) more than 50% of the mass of the external holding magnet is located on a side of the middle plane at which the innermost surface is located, wherein the edges of the external holding magnet at the outer end surface are chamfered.

23. The implant system according to claim 12, wherein the implant device is a hearing implant device.

24. The implant system according to claim 23, wherein the hearing implant device is a cochlear implant.

\* \* \* \* \*